(12) United States Patent
Lo et al.

(10) Patent No.: US 9,982,300 B2
(45) Date of Patent: *May 29, 2018

(54) SIZE-BASED GENOMIC ANALYSIS

(71) Applicant: The Chinese University of Hong Kong, Shatin, New Territories (CN)

(72) Inventors: Yuk Ming Dennis Lo, Kowloon (CN);
Kwan Chee Chan, Kowloon (CN);
Wai Kwun Rossa Chiu, Shatin (CN);
Wenli Zheng, New Territories (CN)

(73) Assignee: The Chinese University of Hong Kong, Shatin (HK)

( * ) Notice: Subject to any disclaimer, the term of this patent is extended or adjusted under 35 U.S.C. 154(b) by 730 days.

This patent is subject to a terminal disclaimer.

(21) Appl. No.: 14/089,720

(22) Filed: Nov. 25, 2013

(65) Prior Publication Data

US 2014/0080720 A1 Mar. 20, 2014

Related U.S. Application Data

(63) Continuation of application No. 12/940,992, filed on Nov. 5, 2010, now Pat. No. 8,620,593.

(60) Provisional application No. 61/360,399, filed on Jun. 30, 2010.

(51) Int. Cl.
*C12Q 1/68* (2018.01)
*G06F 19/18* (2011.01)

(52) U.S. Cl.
CPC ........ *C12Q 1/6883* (2013.01); *C12Q 1/6809* (2013.01); *G06F 19/18* (2013.01); *C12Q 2600/112* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| 8,620,593 | B2* | 12/2013 | Lo | ........................ | C12Q 1/6809 365/94 |
|---|---|---|---|---|---|
| 2005/0164241 | A1 | 7/2005 | Hahn | | |
| 2007/0122823 | A1 | 5/2007 | Bianchi | | |
| 2007/0202525 | A1 | 8/2007 | Quake | | |
| 2009/0029377 | A1 | 1/2009 | Lo | | |

FOREIGN PATENT DOCUMENTS

| WO | 2004/078999 | | 9/2004 |
| WO | 2007/028155 | | 3/2007 |
| WO | 2007/100911 | | 9/2007 |
| WO | 2009/013492 | | 1/2009 |
| WO | 2009/013496 | A1 | 1/2009 |

OTHER PUBLICATIONS

Korbel et al. Paired-End Mapping Reveals Extensive Structural Variation in the Human Genome Science vol. 318, pp. 420-426 (2007).*
Partial English Translation of Office Action dated Sep. 10, 2014 in Chinese Patent Application No. 201080059269.7, 3 pages.
Ding, Chunming, et al., "MS Analysis of Single-Nucleotide Differences in Circulating Nucleic Acids: Application to Noninvasive Prenatal Diagnosis," Jul. 20, 2004, Proceedings of the National Academy of Sciences of the United States of America, vol. 101, No. 29, pp. 10762-10767.
Reed, W., et al., "Non-Invasive Determination of the Paternal HLA Haplotype of a Fetus Using Kinetic PCR to Detect Fetal Microchimerism in Maternal Plasma," Mar. 2, 2002, Bone Marrow Transplantation, vol. 29, No. 6, pp. 527-529.
Chiu, Rossa, W.K., et al., "Non-Invasive Prenatal Diagnosis by Single Molecule Counting Technologies," Jul. 1, 2009, Trends in Genetics, vol. 25, No. 7, pp. 324-331.
Lun, Fiona, M.F., et al., "Noninvasive Prenatal Diagnosis of Monogenic Diseases by Digital Size Selection and Relative Mutation Dosage on DNA in Maternal Plasma," Dec. 16, 2008, Proceedings of the National Academy of Sciences of the United States of America, vol. 105, No. 50, pp. 19920-19925.
Fan, H., Christina, et al., "Noninvasive Diagnosis of Fetal Aneuploidy by Shotgun Sequencing DNA from Maternal Blood," Oct. 21, 2008, Proceedings of the National Academy of Sciences of the United States of America, vol. 105, No. 42, pp. 16266-16271.
Chiu, Rossa, W.K., et al., "Noninvasive Prenatal Diagnosis of Fetal Chromosomal Aneuploidy by Massively Parallel Genomic Sequencing of DNA in Maternal Plasma," Dec. 23, 2008, Proceedings of the National Academy of Sciences of the United States of America, vol. 105, No. 51, pp. 20458-20463.
Larrabee, Paige, B., et al., "Microarray Analysis of Cell-Free Fetal DNA in Amniotic Fluid: A Prenatal Molecular Karyotype," Sep. 1, 2004, American Journal of Human Genetics, vol. 75, No. 3, pp. 485-491.

(Continued)

*Primary Examiner* — John S. Brusca
(74) *Attorney, Agent, or Firm* — Kilpatrick Townsend & Stockton LLP

(57) ABSTRACT

Systems, methods, and apparatuses for performing a prenatal diagnosis of a sequence imbalance are provided. A shift (e.g. to a smaller size distribution) can signify an imbalance in certain circumstances. For example, a size distribution of fragments of nucleic acids from an at-risk chromosome can be used to determine a fetal chromosomal aneuploidy. A size ranking of different chromosomes can be used to determine changes of a rank of an at-risk chromosome from an expected ranking. Also, a difference between a statistical size value for one chromosome can be compared to a statistical size value of another chromosome to identify a significant shift in size. A genotype and haplotype of the fetus may also be determined using a size distribution to determine whether a sequence imbalance occurs in a maternal sample relative to a genotypes or haplotype of the mother, thereby providing a genotype or haplotype of the fetus.

15 Claims, 33 Drawing Sheets

(56) References Cited

OTHER PUBLICATIONS

Li, Ying, et al., "Size Separation of Circulatory DNA in Maternal Plasma Permits Ready Detection of Fetal DNA Polymorphisms," Jun. 1, 2004, Clinical Chemistry, American Association for Clinical Chemistry, vol. 50, No. 6, pp. 1002-1011.

Lo, Y. M. Dennis, et al., "Digital PCR for the Molecular Detection of Fetal Chromosomal Aneuploidy," Aug. 2007, Proceedings of the National Academy of Sciences of the United States of America, vol. 104, No. 32, pp. 13116-13121.

Peter, Inga, PhD., et al., "Cell-Free DNA Fragmentation Patters in Amniotic Fluid Identify Genetic Abnormalities and Changes due to Storage," Sep. 2008, Diagn. Mol. Pathol., vol. 17, No. 3, pp. 185-190.

Lapaire, Olav, et al., "Larger Columns and Change of Lysis Buffer Increase the Yield of Cell-Free DNA Extracted from Amniotic Fluid," 2006, Letters to the Editor, Clinical Chemisry, vol. 52, No. 1, pp. 156-157.

Lapaire, Olav, et al., "Cell-Free Fetal DNA in Amniotic Fluid: Unique Fragmentation Signatures in Euploid and Aneuploid Fetuses," 2007, Clinical Chemistry, vol. 53, No. 3, pp. 405-411.

Lapaire, Olav, et al., "Array-CGH Analysis of Cell-Free Fetal DNA in 10 mL of Amniotic Fluid Supernatant," May 17, 2007, Prenatal Diagnosis, vol. 27, pp. 616-621.

Bianchi, Diana, W., et al., "Large Amounts of Cell-Free DNA are Present in Amniotic Fluid," 2001, Clinical Chemistry, vol. 47, No. 10, pp. 1867-1869.

Lecoeur, Nerve, "Nuclear Apoptosis Detection by Flow Cytometry: Influence of Endogenous Endonucleases," 2002, Experimental Cell Research, vol. 277, pp. 1-14.

International Search Report and Written Opinion, dated Apr. 20, 2011, PCT Application No. PCT/US2010/055655, International Filing Date Nov. 6, 2010, 20 pages.

International Search Report and Written Opinion, dated Feb. 23, 2011, PCT/EP2010/066935, International Filing Date Nov. 5, 2010, pp. 13 pages.

Lo, Y.M. Dennis, et al., "Maternal Plasma DNA Sequencing Reveals the Genome-Wide Genetic and Mutational Profile of the Fetus," Dec. 8, 2010, Science Translational Medicine, vol. 2, Issue 61, 14 pages, [on line], retrieved from the internet URL: www.stm.sciencemag.org.

Fan, H., Christina and Quake, Stephen, R., "Detection of Aneuploidy with Digital Polymerase Chain Reaction," Analytical Chemistry, 2007, 4 pages.

Chan, K.C. Allen, et al., Size Distributions of Maternal and Fetal DNA in Maternal Plasma, Clinical Chemistry, 2004, 5 pages. vol. 50 pp. 88-92.

Eurasian Office Action (English Translation) dated Dec. 13, 2013 in EA Patent Application No. 201200701, 3 pages.

Fan, H. Christina et al.; "Analysis of the Size Distributions of Fetal and Maternal Cell-Free DNA by Paired-End Sequencing"; Clinical Chemistry; 2010; 56:8; pp. 1279-1286.

Lo, Y M Dennis et al.; "Plasma placental RNA allelic ratio permits noninvasive prenatal chromosomal aneuploidy detection"; Nature Medicine; Advance Online Publication; Jan. 7, 2007; doi:10.1038/nm1530; 6 pages.

Tong, Yu K. et al.; "Noninvasive Prenatal Detection of Fetal Trisomy 18 by Epigenetic Allelic Ratio Analysis in Maternal Plasma: Theoretical and Empirical Considerations"; Clinical Chemistry; 2006; 52:12; pp. 2194-2202.

\* cited by examiner

| Sample name | Trimester | Fetal karyotype | Mean size of chr21 fragments | Mean size of chr 7 fragments | Difference between means of chr7 & chr21 | P value * (chr7 vs. chr21) | Mean size of chr 14 fragments | Difference between means of chr14 & chr21 | P value * (chr14 vs. chr21) |
|---|---|---|---|---|---|---|---|---|---|
| M4800-male | 3rd | Euploid | 156.2 | 157.0 | 0.8 | 0.08 | 156.1 | -0.1 | 0.822 |
| M4801-male | 3rd | Euploid | 151.2 | 151.7 | 0.5 | 0.085 | 151.5 | 0.3 | 0.564 |
| M4814-female | 3rd | Euploid | 157.8 | 157.3 | -0.5 | 0.106 | 156.8 | -0.9 | 0.022 |
| PW006-Eu-Male | 1st | Euploid | 146.0 | 146.1 | 0.0 | 0.527 | 145.9 | -0.1 | 0.988 |
| PW007-Eu-Male | 1st | Euploid | 152.1 | 152.7 | 0.6 | 0.033 | 152.3 | 0.2 | 0.679 |
| PW008-Eu-Male | 1st | Euploid | 147.2 | 147.3 | 0.1 | 0.538 | 147.0 | -0.2 | 0.688 |
| PW012- Eu- Male | 1st | Euploid | 146.7 | 146.8 | 0.1 | 0.333 | 146.7 | 0.1 | 0.68 |
| PW020- Eu- Male | 1st | Euploid | 139.7 | 140.0 | 0.3 | 0.174 | 139.7 | 0.0 | 0.741 |
| PW009-Eu-Female | 1st | Euploid | 151.9 | 152.2 | 0.3 | 0.068 | 152.1 | 0.2 | 0.405 |
| PW010-Eu-Female | 1st | Euploid | 148.3 | 148.5 | 0.2 | 0.101 | 148.4 | 0.1 | 0.286 |
| PW016- Eu-Female | 1st | Euploid | 141.5 | 141.1 | -0.4 | 0.782 | 141.2 | -0.3 | 0.842 |
| PW022- Eu-Female | 1st | Euploid | 140.8 | 140.7 | -0.1 | 0.362 | 140.5 | -0.4 | 0.94 |
| M2849- T21- Male | 1st | T21 | 145.9 | 147.0 | 1.1 | <0.001 | 146.8 | 0.8 | <0.001 |
| M4386- T21- Male | 1st | T21 | 144.3 | 146.3 | 2.0 | <0.001 | 145.9 | 1.6 | <0.001 |
| M4467-T21-Male | 1st | T21 | 141.0 | 142.7 | 1.7 | <0.001 | 142.3 | 1.3 | <0.001 |
| M4620-T21-Male | 1st | T21 | 149.7 | 151.3 | 1.6 | <0.001 | 150.9 | 1.2 | <0.001 |

|  | Number of cases | | |
|---|---|---|---|
|  | Female | Male | Total |
| Trisomy 13 (T13) | 9 | 14 | 23 |
| Trisomy 18 (T18) | 20 | 10 | 30 |
| Trisomy 21 (T21) | 4 | 5 | 9 |
| Euploid | 23 | 35 | 58 |
| Total | 56 | 64 | 120 |

FIG. 11
1100

| Sample name | Karyotype | Mean size of chr13 fragments | Mean size of chr 5 fragments | Difference between means of chr 5 & chr 13 | P value * (chr5 vs. chr13) | Mean size of chr 6 fragments | Difference between means of chr 6 & chr 13 | P value * (chr 6 vs. chr13) |
|---|---|---|---|---|---|---|---|---|
| 87164 - Eu - Male | Euploid | 154.969 | 155.198 | 0.229 | 0.159 | 155.037 | 0.068 | 0.732 |
| 87213 - Eu - Male | Euploid | 154.965 | 155.294 | 0.329 | 0.09 | 155.339 | 0.374 | 0.256 |
| 94355 - T18 - Male | Trisomy 18 | 163.908 | 164.11 | 0.202 | 0.035 | 164.143 | 0.235 | 0.276 |
| 96233 - T18 - Male | Trisomy 18 | 163.751 | 164.074 | 0.323 | 0.356 | 163.623 | -0.128 | 0.371 |
| 92394 - T13 - Male | Trisomy 13 | 165.15 | 165.754 | 0.604 | <0.001 | 165.901 | 0.751 | <0.001 |
| 61175 - T13 - Male | Trisomy 13 | 156.165 | 156.581 | 0.416 | <0.001 | 156.696 | 0.531 | <0.001 |
| 96342 - T13 - Female | Trisomy 13 | 157.064 | 158.127 | 1.063 | <0.001 | 158.301 | 1.237 | <0.001 |
| PW093 - T13 - Female | Trisomy 13 | 159.038 | 159.846 | 0.808 | <0.001 | 159.679 | 0.641 | 0.001 |

| Sample name | Karyotype | Mean size of chr 18 fragments | Mean size of chr 14 fragments | Difference between means of chr 18 & chr 14 | P value (chr18 vs. chr14) |
|---|---|---|---|---|---|
| 87164- Eu- Male | Euploid | 155.595 | 154.614 | 0.981 | <0.001 |
| 87213- Eu- Male | Euploid | 155.977 | 155.142 | 0.835 | <0.001 |
| 94355- T18- Male | Trisomy 18 | 163.637 | 163.914 | -0.277 | 0.541 |
| 96233- T18- Male | Trisomy 18 | 163.897 | 164.378 | -0.481 | 0.393 |
| 92394- T13- Male | Trisomy 13 | 166.163 | 165.715 | 0.448 | <0.001 |
| 61175- T13- Male | Trisomy 13 | 157.186 | 156.606 | 0.58 | <0.001 |
| 96342- T13- Female | Trisomy 13 | 158.326 | 158.013 | 0.313 | 0.003 |
| PW093- T13- Female | Trisomy 13 | 160.469 | 159.503 | 0.966 | <0.001 |

| Chr. | GC content (%) |
|---|---|
| 4 | 36.53 |
| 13 | 37.10 |
| 6 | 38.60 |
| 5 | 38.61 |
| 3 | 38.79 |
| X | 38.96 |
| 18 | 39.07 |
| 8 | 39.45 |
| 2 | 39.67 |
| 12 | 39.80 |
| 7 | 39.94 |
| 21 | 40.00 |
| 14 | 40.33 |
| 9 | 41.03 |
| 10 | 41.41 |
| 1 | 41.52 |
| 11 | 41.89 |
| 15 | 42.35 |
| 20 | 44.65 |
| 16 | 45.22 |
| 17 | 46.05 |
| 22 | 49.89 |
| 19 | 50.65 |

FIG. 20

| Sample ID | Karyotype | Z-score for chr 18 | Z-score for chr 13 | Significant shortening of chr 18 DNA fragments detected | Significant shortening of chr 13 DNA fragments detected |
|---|---|---|---|---|---|
| 1 | Euploid | 1.07 | 0.84 | no | no |
| 2 | Euploid | -0.64 | 0.08 | no | no |
| 3 | Trisomy 18 | 3.62 | -1.43 | yes | no |
| 4 | Trisomy 18 | 6.07 | 0.51 | yes | no |
| 5 | Trisomy 13 | 0.61 | 3.55 | no | yes |
| 6 | Trisomy 13 | -1.04 | 2.06 | no | yes |
| 7 | Trisomy 13 | 2.67 | 5.72 | no | yes |
| 8 | Trisomy 13 | -1.39 | 1.55 | no | yes |

FIG. 24

| Type α SNPs ||||||
|---|---|---|---|---|---|
| No of SNPs in the segment | Starting SNP | Ending SNP | Fraction of total length contributed by short fragments || $\Delta F_{(Hap\ I\ -\ Hap\ II)}$ |
| | | | Hap I | Hap II | |
| 50 | rs2027649 | rs5993883 | 0.2595 | 0.2096 | 0.0499 |
| 50 | rs2239395 | rs1002286 | 0.2648 | 0.2219 | 0.0429 |
| 50 | rs4822458 | rs3747134 | 0.2905 | 0.2204 | 0.0701 |
| 50 | rs5761557 | rs4410 | 0.2659 | 0.2037 | 0.0623 |
| 50 | rs134784 | rs4822998 | 0.2569 | 0.2221 | 0.0348 |
| 50 | rs5762936 | rs5998473 | 0.2882 | 0.2302 | 0.0580 |
| 50 | rs5754086 | rs8140669 | 0.2599 | 0.2311 | 0.0288 |
| 50 | rs5999854 | rs5756540 | 0.2659 | 0.2249 | 0.0411 |
| 50 | rs229535 | rs2413637 | 0.2953 | 0.2425 | 0.0528 |
| 50 | rs4820431 | rs11090087 | 0.2793 | 0.2199 | 0.0594 |
| 50 | rs1023469 | rs1972489 | 0.2884 | 0.2438 | 0.0445 |
| 50 | rs5764858 | rs5769218 | 0.2644 | 0.2001 | 0.0643 |
| 50 | rs6009043 | rs5769452 | 0.2481 | 0.2118 | 0.0363 |
| 28 | rs17825762 | rs131815 | 0.2648 | 0.2407 | 0.0241 |

FIG. 28

| Type β SNPs ||||||
|---|---|---|---|---|---|
| No of SNPs in the segment | Starting SNP | Ending SNP | Fraction of total length contributed by short fragments || $\Delta F_{(Hap\ I\ -\ Hap\ II)}$ |
| | | | Hap I | Hap II | |
| 50 | rs2159071 | rs873387 | 0.2565 | 0.2414 | 0.0151 |
| 50 | rs11917 | rs78908 | 0.2548 | 0.2577 | -0.0029 |
| 50 | rs589089 | rs7288450 | 0.2495 | 0.2589 | -0.0093 |
| 50 | rs5759868 | rs2301492 | 0.2431 | 0.2477 | -0.0046 |
| 50 | rs2301497 | rs713911 | 0.2411 | 0.2204 | 0.0207 |
| 50 | rs4820740 | rs5752850 | 0.2181 | 0.2195 | -0.0014 |
| 50 | rs5752851 | rs5752964 | 0.2344 | 0.2372 | -0.0028 |
| 50 | rs1894473 | rs135472 | 0.2603 | 0.2510 | 0.0093 |
| 50 | rs135475 | rs5754558 | 0.2324 | 0.2457 | -0.0133 |
| 50 | rs4821148 | rs11705488 | 0.2381 | 0.2380 | 0.0001 |
| 50 | rs390647 | rs362246 | 0.2270 | 0.2224 | 0.0046 |
| 50 | rs362214 | rs6000130 | 0.2404 | 0.2401 | 0.0003 |
| 50 | rs739206 | rs12628179 | 0.2341 | 0.2193 | 0.0148 |
| 50 | rs17298479 | rs2143921 | 0.2597 | 0.2643 | -0.0047 |
| 50 | rs5758913 | rs926542 | 0.2655 | 0.2582 | 0.0073 |
| 50 | rs7291629 | rs133761 | 0.2156 | 0.2360 | -0.0203 |
| 50 | rs133755 | rs6007919 | 0.2359 | 0.2332 | 0.0027 |
| 50 | rs135570 | rs136646 | 0.2496 | 0.2466 | 0.0030 |
| 50 | rs80454 | rs8136986 | 0.2354 | 0.2372 | -0.0018 |
| 50 | rs5768117 | rs133662 | 0.2339 | 0.2330 | 0.0009 |
| 49 | rs6007851 | rs739365 | 0.2376 | 0.2372 | 0.0004 |

FIG. 29

| Sample code | Target enrichment | Fetal status | Total length contributed by DNA fragments of ≤150 bp for chromosome 21 (million bp) | Total length contributed by DNA fragments of ≤600 bp for chromosome 21 (million bp) | $F_{21}$ | Total length contributed by DNA fragments of ≤150 bp for reference chromosomes (million bp) | Total length contributed by DNA fragments of ≤600 bp for reference chromosomes (million bp) | $F_{ref}$ | $\Delta F$ |
|---|---|---|---|---|---|---|---|---|---|
| uk 99229 | No | T21 | 10.2 | 36.0 | 0.283 | 653.1 | 2422.2 | 0.270 | 0.013 |
| pw 421 | No | T21 | 10.6 | 35.6 | 0.299 | 651.2 | 2315.5 | 0.281 | 0.018 |
| uk 99510 | No | T21 | 9.8 | 32.0 | 0.307 | 607.1 | 2082.2 | 0.292 | 0.016 |
| uk 99807 | No | T21 | 12.6 | 30.1 | 0.417 | 745.2 | 1905.8 | 0.391 | 0.026 |
| pw 226 | No | euploid | 10.4 | 33.7 | 0.310 | 734.7 | 2368.4 | 0.310 | 0.000 |
| pw 316 | No | euploid | 10.9 | 38.4 | 0.284 | 765.2 | 2691.8 | 0.284 | 0.000 |
| pw 263 | No | euploid | 7.7 | 25.9 | 0.297 | 537.5 | 1810.8 | 0.297 | 0.001 |
| pw 370 | No | euploid | 5.9 | 23.9 | 0.247 | 411.8 | 1671.0 | 0.246 | 0.000 |

FIG. 31A

| Sample code | Target enrichment | Fetal status | Total length contributed by DNA fragments of ≤150 bp for chromosome 21 (million bp) | Total length contributed by DNA fragments of ≤600 bp for chromosome 21 (million bp) | $F_{21}$ | Total length contributed by DNA fragments of ≤150 bp for reference chromosomes (million bp) | Total length contributed by DNA fragments of ≤600 bp for reference chromosomes (million bp) | $F_{ref}$ | $\Delta F$ |
|---|---|---|---|---|---|---|---|---|---|
| uk 99229 | Yes | T21 | 5.7 | 24.9 | 0.231 | 434.1 | 1938.3 | 0.224 | 0.007 |
| pw 421 | Yes | T21 | 5.1 | 22.4 | 0.226 | 362.4 | 1685.0 | 0.215 | 0.011 |
| uk 99510 | Yes | T21 | 4.4 | 19.0 | 0.229 | 314.4 | 1435.1 | 0.219 | 0.010 |
| uk 99807 | Yes | T21 | 6.6 | 21.3 | 0.312 | 455.1 | 1553.2 | 0.293 | 0.019 |
| pw 226 | Yes | euploid | 5.1 | 21.4 | 0.237 | 413.2 | 1720.2 | 0.240 | -0.004 |
| pw 316 | Yes | euploid | 4.9 | 22.6 | 0.215 | 394.9 | 1811.5 | 0.218 | -0.003 |
| pw 263 | Yes | euploid | 4.1 | 19.3 | 0.211 | 327.0 | 1526.6 | 0.214 | -0.004 |
| pw 370 | Yes | euploid | 3.7 | 20.4 | 0.180 | 296.9 | 1621.0 | 0.183 | -0.003 |

FIG. 31B

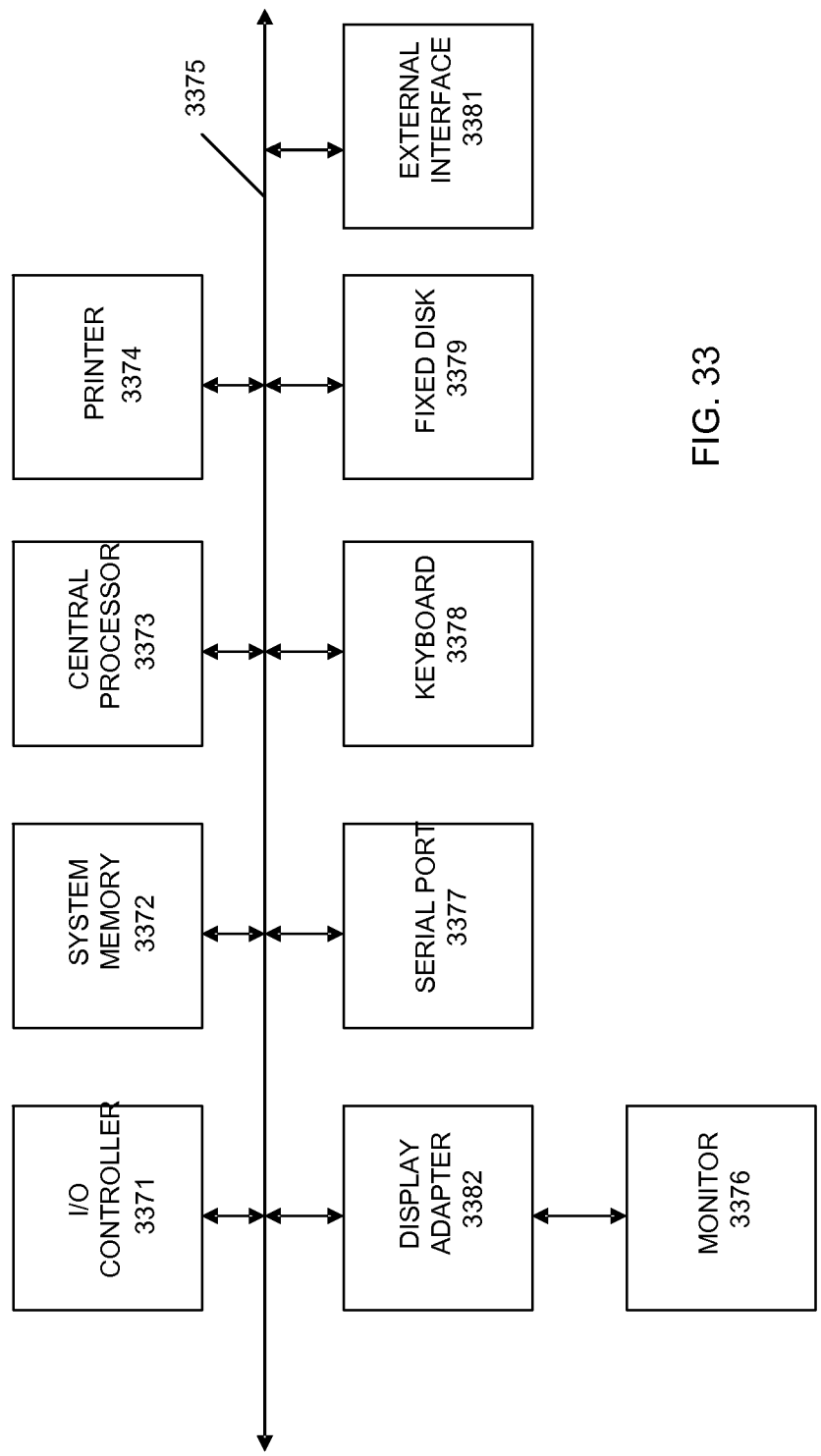

SIZE-BASED GENOMIC ANALYSIS

CROSS-REFERENCES TO RELATED APPLICATIONS

The present application is a continuation of U.S. application Ser. No. 12/940,992, entitled "SIZE-BASED GENOMIC ANALYSIS" filed Nov. 5, 2010, which claims priority from and is a non-provisional application of U.S. Provisional Application No. 61/360,399, entitled "Size-Based Genomic Analysis" filed Jun. 30, 2010, the entire contents of which are herein incorporated by reference for all purposes.

The present application is also related to U.S. application Ser. No. 12/178,181, entitled "Diagnosing Fetal Chromosomal Aneuploidy Using Massively Parallel Genomic Sequencing," filed Jul. 23, 2008; U.S. application Ser. No. 12/614,350, entitled "Diagnosing Fetal Chromosomal Aneuploidy Using Genomic Sequencing With Enrichment," filed Nov. 6, 2009, and U.S. application Ser. No. 12/940,993, entitled "Fetal Genomic Analysis From A Maternal Biological Sample," filed on Nov. 5, 2010, the entire contents of which are herein incorporated by reference for all purposes.

BACKGROUND

The discovery of fetal DNA in maternal plasma in 1997 has opened up new possibilities for noninvasive prenatal diagnosis (Lo et al Lancet 1997; 350: 485-487). This technology has been rapidly translated to clinical applications, with the detection of fetal-derived, paternally-inherited genes or sequences, e.g. for fetal sex determination and for fetal RhD status determination. However, prenatal diagnostic applications involving genomic targets which are present in both the maternal and fetal genomes, e.g., chromosome 21, are much more challenging.

Recently, it has been demonstrated that single molecule counting techniques, with their superior quantitative precision, might be a promising solution for this problem (Lo et al Proc Natl Acad Sci USA 2007; 104: 13116-13121; Fan et al Anal Chem 2007; 79: 7576-7579; U.S. patent application Ser. No. 11/701,686; Chiu et al Trends Genet 2009; 25: 324-331; Chiu et al Proc Natl Acad Sci USA 2008; 105: 20458-20463; Fan et al Proc Natl Acad Sci USA 2008; 105: 16266-16271). Such methods achieve diagnostic goals through the observation of quantitative differences in the number of molecules from selected genomic locations between disease and health. For example, for the diagnosis of fetal Down syndrome, the number of molecules from chromosome 21 will be increased when the fetus is suffering from trisomy 21 (Chiu et al Proc Natl Acad Sci USA 2008; 105: 20458-20463; Fan et al Proc Natl Acad Sci USA 2008; 105: 16266-16271).

However, such counting techniques may suffer from a limited number of data points or other disadvantages. Therefore, it is desirable to provide new methods, systems, and apparatus for performing prenatal diagnosis having certain advantages over existing techniques.

BRIEF SUMMARY

Certain embodiments of the present invention can provide systems, methods, and apparatus can use a size-based analysis to perform a prenatal diagnosis of a sequence imbalance (e.g. a fetal chromosomal aneuploidy) in a biological sample obtained from a pregnant female subject. For example, a size distribution of fragments of nucleic acid molecules for an at-risk chromosome can be used to determine a fetal chromosomal aneuploidy. Some embodiments can also detect other sequence imbalances, such as a sequence imbalance in the biological sample (containing mother and fetal DNA), where the imbalance is relative to a genotype, mutation status, or haplotype of the mother. Such an imbalance can be determined via a size distribution of fragments (nucleic acid molecules) corresponding to a particular sequence relative to a size distribution to be expected if the sample were purely from the mother, and not from the fetus and mother. A shift (e.g. to a smaller size distribution) can signify an imbalance in certain circumstances.

In one embodiment, a ranking of a size distribution (e.g. a statistical value representing a size distribution) of fragments from respective chromosomes relative to each other are used to determine an imbalance. For instance, a ranking of the size of fragments of the at-risk chromosome in the test sample can be compared to the ranking for the at-risk chromosome that was obtained from a reference biological sample. A diagnosis can be performed based on the comparison. As an example, if the ranking changes (e.g. indicating a reduction in size of the nucleic acid fragments) by a specified amount then a diagnosis that a fetal chromosomal aneuploidy exists in the at-risk chromosome may be made. In various embodiments using such ranking analysis, all 22 autosomes and the sex chromosomes can be used, or a subset of the chromosomes can be used.

In another embodiment, a difference between a size (e.g. a statistical value representing a size distribution) of the fragments of the at-risk chromosome and a size of the fragments of a reference chromosome is used. For example, if the difference in the size is greater or smaller than a cutoff (also called a threshold), then a diagnosis that a fetal chromosomal aneuploidy exists in the at-risk chromosome can be made.

According to one example embodiment, a method for performing prenatal diagnosis of a sequence imbalance in a biological sample obtained from a pregnant female subject is provided. The biological sample includes nucleic acid molecules that are part of nucleic acid sequences. For each of a plurality of the nucleic acid molecules in the biological sample, a size of the nucleic acid molecule is measured, and from which nucleic acid sequence the nucleic acid molecule derives is identified. A computer system determines a size distribution of the nucleic acid molecules corresponding to a first sequence. Based on the determined size distribution, a classification of whether a sequence imbalance exists for the first sequence is determined.

According to another example embodiment, a method for performing prenatal diagnosis of a fetal chromosomal aneuploidy in a biological sample obtained from a pregnant female subject is provided. For each of a plurality of the nucleic acid molecules in the biological sample, a size of the nucleic acid molecule is measured, and from which chromosome the nucleic acid molecule derives is identified. A computer system calculates a statistical value from the sizes of nucleic acid molecules corresponding to a chromosome. A statistical value is calculated for each of a plurality of chromosomes. A ranking of the chromosomes is determined based on the statistical value. The determined ranking of a first chromosome is compared to another ranking of the first chromosome obtained from a reference biological sample. Based on the comparison, a classification of whether a fetal chromosomal aneuploidy exists for the first chromosome is determined.

According to another example embodiment, a method for performing prenatal diagnosis of a fetal chromosomal aneuploidy in a biological sample obtained from a pregnant female subject is provided. For each of a plurality of the nucleic acid molecules in the biological sample, a size of the nucleic acid molecule is measured, and from which chromosome the nucleic acid molecule derives is identified. A computer system calculates a first statistical value from the sizes of nucleic acid molecules corresponding to a first chromosome. The computer system calculates a second statistical value from the sizes of nucleic acid molecules corresponding to one or more second chromosomes. A separation value between the first statistical value and the second statistical value is determined. The separation value is compared to one or more cutoff values. Based on the comparison, a classification of whether a fetal chromosomal aneuploidy exists for the first chromosome is determined.

Other embodiments of the invention are directed to systems and computer readable media associated with methods described herein. In one embodiment, the computer readable medium contains instructions for receiving data and analyzing data, but not instructions for directing a machine to create the data (e.g. sequencing nucleic acid molecules). In another embodiment, the computer readable medium does contain instructions for directing a machine to create the data. In one embodiment, a computer program product comprises a computer readable medium storing a plurality of instructions for controlling a processor to perform an operation for methods described herein. Embodiments are also directed to computer systems configured to perform the steps of any of the methods described herein, potentially with different components performing a respective step or a respective group of steps.

Reference to the remaining portions of the specification, including the drawings and claims, will realize other features and advantages of embodiments of the present invention. Further features and advantages, as well as the structure and operation of various embodiments of the present invention, are described in detail below with respect to the accompanying drawings. In the drawings, like reference numbers can indicate identical or functionally similar elements.

BRIEF DESCRIPTION OF THE DRAWINGS

FIG. 5 is a table illustrating comparisons of chromosome 21 to chromosome 7 and chromosome 14 in terms of the size of sequences aligned to them according to embodiments of the present invention.

FIG. 11 shows a table 1100 for the gender and classification of 120 pregnancies according to embodiments of the present invention.

FIG. 16 is a table illustrating comparisons of chromosome 13 to chromosome 5 and chromosome 6 in terms of the size of sequences aligned to them according to embodiments of the present invention. The comparisons of chromosomes 5 and 6 with chromosome 13 are used for the detection of changes in the size of chromosome 21 sequences in trisomy 13 pregnancies. Results from euploid and trisomy 18 pregnancies are included for comparison.

FIG. 17 is a table illustrating comparisons of chromosome 18 to chromosome 12 and chromosome 14 in terms of the size of sequences aligned to them according to embodiments of the present invention. Results from euploid and trisomy 13 pregnancies are included for comparison according to embodiments of the present invention.

FIG. 20 shows a list of the GC contents of different chromosomes (NCBI build 36, version 48) according to embodiments of the present invention.

FIG. 24 shows a comparison of the accuracies of an embodiment of the present invention and another method for the noninvasive detection of fetal aneuploidies (trisomy 13 and trisomy 18) using maternal plasma DNA analysis.

FIG. 28 shows a table illustrating a size analysis for type α single-nucleotide polymorphisms (SNPs) on chromosome 22 according to embodiments of the present invention.

FIG. 29 shows a table illustrating a size analysis for type β SNPs on chromosome 22 according to embodiments of the present invention.

FIG. 31A is a table that provides a size analysis of plasma DNA without target enrichment according to embodiments of the present invention.

FIG. 31B is a table that provides a size analysis of plasma DNA with target enrichment according to embodiments of the present invention.

FIG. 33 shows a block diagram of an exemplary computer apparatus usable with system and methods according to embodiments of the present invention.

DEFINITIONS

Figure 1:
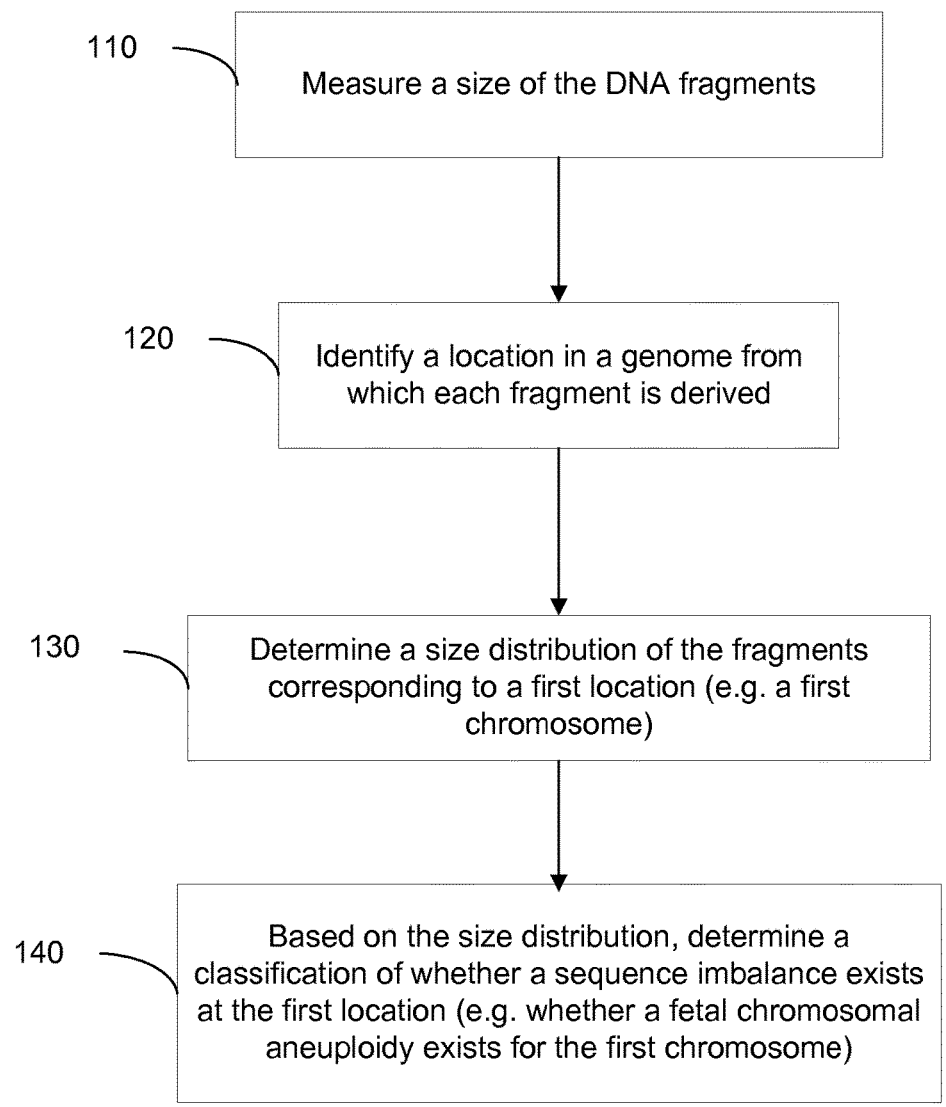
FIG. 1 is a flowchart illustrating a method 100 of performing prenatal diagnosis of a sequence imbalance in a biological sample obtained from a pregnant female subject according to embodiments of the present invention.

The term "biological sample" as used herein refers to any sample that is taken from a subject (e.g., a human, such as a pregnant woman) and contains one or more nucleic acid molecule(s) of interest.

The term "nucleic acid" or "polynucleotide" refers to a deoxyribonucleic acid (DNA) or ribonucleic acid (RNA) and a polymer thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, copy number variants, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, mRNA, small noncoding RNA, micro RNA (miRNA), Piwi-interacting RNA, and short hairpin RNA (shRNA) encoded by a gene or locus.

The term "gene" means the segment of DNA involved in producing a polypeptide chain or transcribed RNA product. It may include regions preceding and following the coding region (leader and trailer) as well as intervening sequences (introns) between individual coding segments (exons).

The term "clinically relevant nucleic acid sequence" (also referred to as a target sequence or chromosome) as used herein can refer to a polynucleotide sequence corresponding to a segment of a larger genomic sequence whose potential imbalance is being tested or to the larger genomic sequence itself. One example is the sequence of chromosome 21. Other examples include chromosome 18, 13, X and Y. Yet other examples include mutated genetic sequences or genetic polymorphisms or copy number variations that a fetus may inherit from one or both of its parents, or as a de novo mutation in the fetus. In some embodiments, multiple clinically relevant nucleic acid sequences, or equivalently multiple markers of the clinically relevant nucleic acid sequence, can be used to provide data for detecting the imbalance. For instance, data from five non-consecutive sequences on chromosome 21 can be used in an additive fashion for the determination of possible chromosomal 21 imbalance, effectively reducing the needed sample volume to ⅕.

The term "reference nucleic acid sequence" as used herein refers to a nucleic acid sequence whose size distribution is used to compare against the target sequence. Examples of a reference nucleic acid sequence include a chromosome, a part of a chromosome, a particular allele (e.g. of a mother), a particular haplotype, a genome, or an artificially synthesized nucleic acid sequence. Such reference nucleic acid sequences can either exist endogenously in the sample, or added exogenously during sample processing or analysis. In some embodiments, the reference nucleic acid sequences demonstrate a size profile that is representative of a healthy state without disease.

The term "based on" as used herein means "based at least in part on" and refers to one value (or result) being used in the determination of another value, such as occurs in the relationship of an input of a method and the output of that method. The term "derive" as used herein also refers to the relationship of an input of a method and the output of that method, such as occurs when the derivation is the calculation of a formula.

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter.

As used herein, the term "locus" or its plural form "loci" is a location or address of any length of nucleotides (or base pairs) which has a variation across genomes.

The term "sequence imbalance" as used herein means any significant deviation as defined by at least one cutoff value in a quantity of the clinically relevant nucleic acid sequence from a reference quantity. A sequence imbalance can include chromosome dosage imbalance, allelic imbalance, mutation dosage imbalance, copy number imbalance, haplotype dosage imbalance, and other similar imbalances. As an example, an allelic or mutation dosage imbalance can occur when a fetus has a different genotype from the mother, thereby creating an imbalance at a particular locus in the sample.

The term "chromosomal aneuploidy" as used herein means a variation in the quantitative amount of a chromosome from that of a diploid genome. The variation may be a gain or a loss. It may involve the whole of one chromosome or a region of a chromosome.

The term "haplotype" as used herein refers to a combination of alleles at multiple loci that are transmitted together on the same chromosome or chromosomal region. A haplotype may refer to as few as one pair of loci or to a chromosomal region, or to an entire chromosome. The term "alleles" refers to alternative DNA sequences at the same physical genomic locus, which may or may not result in different phenotypic traits. In any particular diploid organism, with two copies of each chromosome (except the sex chromosomes in a male human subject), the genotype for each gene comprises the pair of alleles present at that locus, which are the same in homozygotes and different in heterozygotes. A population or species of organisms typically includes multiple alleles at each locus among various individuals. A genomic locus where more than one allele is found in the population is termed a polymorphic site. Allelic variation at a locus is measurable as the number of alleles (i.e., the degree of polymorphism) present, or the proportion of heterozygotes (i.e., the heterozygosity rate) in the population. As used herein, the term "polymorphism" refers to any inter-individual variation in the human genome, regardless of its frequency. Examples of such variations include, but are not limited to, single nucleotide polymorphism, simple tandem repeat polymorphisms, insertion-deletion polymorphisms, mutations (which may be disease causing) and copy number variations.

DETAILED DESCRIPTION

Fetal DNA molecules that are present in the plasma of pregnant women have been found to be generally shorter than maternally-derived molecules (Chan et al Clin Chem 2004; 50: 88-92; Li et al Clin Chem 2004; 50: 1002-1011; US Patent Application 20050164241). Certain embodiments of the present invention can determine from the maternal plasma DNA whether the fetus has over- or under-representation of a particular part of the genome by a change of the size of DNA molecules derived from that part of the genome. As fetal DNA represents a minor fraction of DNA in maternal plasma, the overall degree of size change in maternal plasma is likely to be small, and thus can be difficult to detect. In some embodiments, the sizes of a number of molecules are measured to arrive at a statistically significant difference between disease and health.

I. Determining Size of a Fragment

One method with which the sizes of a number of DNA molecules can be measured is by massively parallel genomic sequencing. This can be performed for example by the Illumina Genome Analyzer platform (using sequencing by synthesis) (Bentley D R et al Nature 2008; 456: 53-59), the ABI SOLiD (using sequencing by ligation) (McKernan et al Genome Res 2009; 19: 1527-1541), the Roche 454 platform (Marguelis et al Nature 2005; 437:376-380) and the Helicos single molecule sequencing platform (Harris et al Science 2008; 320: 106-109). It is also expected that other massively parallel sequencing platforms can also be used, e.g. the Pacific Biosciences (single molecule, real-time (SMRTTM) technology) (Eid et al Science 2009; 323: 133-138), nanopore sequencing (Clarke J et al. Nat Nanotechnol 2009; 4: 465-470), semiconductor sequencing (e.g. by Ion Torrent (iontorrent.com)), etc.

One way to obtain the DNA size information from such sequencing is to perform paired-end (PE) sequencing, in which both ends of a DNA molecule are sequenced. Then, the sequences corresponding to both ends of the molecule can be mapped back to the reference genome (e.g. a reference human genome or a reference horse genome, or the genome of any animal of interest). In one embodiment, both ends are each sequenced at a length that is long enough to be mapped back, individually for each end, to the reference human genome (e.g. about 10-24 bases or 25-36 bases). In another embodiment, only a proportion of sequences can be mapped back without mismatch to the non-repeat region of the human genome. In one aspect, the mapping may be unambiguous if both sequences together are used in the mapping. In this scenario, even though each of the ends might be too short to be mapped back with confidence, using both sequences can provide unambiguous mapping. The size of the molecule can be worked out by subtraction of the genomic coordinates of the ends of the two sequences.

In another embodiment, the size of the molecule can be obtained by a complete, or close to complete, sequencing of the whole DNA molecule, instead of just the two ends. This can be done efficiently by sequencing platforms with relatively long read-lengths, such as the Roche 454 platform, the Pacific Biosciences single molecule, real-time (SM-RTTM) technology, and the Ion Torrent technology (iontorrent.com).

The throughput of the above-mentioned sequencing-based methods can be increased with the use of indexing or barcoding (Cronn et al. Nucleic Acids Res 2008; 36: e122). Thus, a sample or patient-specific index or barcode can be added to nucleic acid fragments in a particular nucleic acid sequencing library. Then, a number of such libraries, each with a sample or patient-specific index or barcode, are mixed together and sequenced together. Following the sequencing reactions, the sequencing data can be harvested from each sample or patient based on the barcode or index. This strategy can increase the throughput and thus the cost-effectiveness of the current invention.

In another embodiment, the nucleic acid molecules in the biological sample can be selected or fractionated prior to size analysis. In one variant, the nucleic acid molecules are treated with a device (e.g. a microarray or a solution containing probes) which would preferentially bind nucleic acid molecules from selected loci in the genome (e.g. one of chromosomes 21, 18, 13, or X), then the size analysis can be performed on the bound subset of the nucleic acid molecules. In such an embodiment, a Nimblegen sequence capture system (nimblegen.com/products/seqcap/index.html) or an Agilent SureSelect Target Enrichment System (opengenomics.com/SureSelect_Target_Enrichment_System), or similar platforms can be used. In another embodiment, the unbound nucleic acid subset can be differentially removed or degraded or digested.

At least some embodiments can work with any single molecule analysis platform in which the chromosomal origin and the length of the molecule can be analyzed, e.g. electrophoresis, optical methods (e.g. optical mapping and its variants, en.wikipedia.org/wiki/Optical_mapping#cite note-Nanocoding-3, and Jo et al. Proc Natl Acad Sci USA 2007; 104: 2673-2678), fluorescence-based method, probe-based methods, digital PCR (microfluidics-based, or emulsion-based, e.g. BEAMing (Dressman et al. Proc Natl Acad Sci USA 2003; 100: 8817-8822), RainDance (raindancetech- .com/technology/per-genomics-research.asp), rolling circle amplification, mass spectrometry, melting analysis (or melting curve analysis), molecular sieving, etc. As an example for mass spectrometry, a longer molecule would have a larger mass (an example of a size value).

In one example, plasma DNA molecules were randomly sequenced by the Illumina Genome Analyzer system using a paired-end sequencing protocol. In this experiment, version 1 of the Illumina Paired-end (PE) Cluster Generation Reagent Kit was used. Each end was sequenced for 36 bp. The two ends of each sequence were aligned to the repeat-masked human genome (NCBI Build 36, version 48) using the eland_pair program in the GAPipeline-1.0 software package provided by Illumina. Only 32 bp out of the 36 bp from each end were used for alignment purposes.

In some embodiments, the PE reads meeting the following criteria can be used for subsequent analysis: (1) the individual members of each suggested pair were both sequenced on the same cluster position on the sequencing flow cell and could be aligned to the same chromosome with the correct orientation as expected for the human reference genome; (2) the sequenced reads of both members of the pair could be aligned to the repeat-masked human reference genome without any nucleotide mismatch; (3) the sequenced reads of each member of the pair had a uniqueness score >4; and (4) pairs demonstrating an insert size less than 600 bp. The size of each aligned sequence was then calculated according to the position of each of the two ends.

II. Using Size Distribution to Determine Aneuploidy Status

FIG. 1 is a flowchart illustrating a method 100 of performing prenatal diagnosis of a sequence imbalance in a biological sample obtained from a pregnant female subject according to embodiments of the present invention. While method 100 is mainly described with respect to analyzing a fetal chromosomal aneuploidy, other embodiments of method 100 and other methods herein can be applied to other sequence imbalances (e.g. identification of genotype or mutations). Method 100 and other methods mentioned herein, may be performed wholly or partially by a computer system including one or more processors.

Method 100 and any of the methods described herein may be totally or partially performed with a computer system including a processor, which can be configured to perform the steps. Thus, embodiments are directed to computer systems configured to perform the steps of any of the methods described herein, potentially with different components performing a respective step or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

In step 110, a size of at least some of the nucleic acid molecules (e.g. DNA or RNA) in the biological sample is measured. The nucleic acid molecules are also referred to as fragments, as they are a fragment of the entire genome. The size may be measured via any suitable method, for example, methods described above.

Step 120 identifies a location in a genome from which each of the nucleic acid molecules is derived. The location can be any part of a genome, which is human for the examples provided, but could be for other genomes. For example, the location can be which chromosome number the fragment is derived, which part of a chromosome as may be defined by genomic coordinates (e.g. a specific coordinate or range of coordinates), and even may be which one of the two chromosomes (assuming euploid) the fragment is derived (originated).

In one embodiment, this identification can be performed by sequencing and comparing the sequence information with the reference human genome sequence. In another embodiment, this identification can be performed by hybridization to a panel of probes with known chromosomal origin. The probes could be labeled with one or more fluorescence labels, in either a microarray format or in solution. In yet another embodiment, the nucleic acid molecules could be captured by a panel of probes, either in solution or on a solid surface, and then the captured (or the remaining non-captured) nucleic acid molecules are sequenced. In some embodiments, where a sequence imbalance other than a chromosomal aneuploidy is to be identified, a step of identifying from which chromosome that a fragment is originated may be optional.

In step 130, a size distribution of the nucleic acid molecules corresponding to a first location (e.g. a first chromosome) is determined Various embodiments can use a variety of size distributions. In some embodiments, a size distribution relates to the rankings of the sizes (e.g., an average, median, or mean) of fragments of one chromosome relative to fragments of other chromosomes. In other embodiments, a size distribution can relate to a statistical value of the actual sizes of the fragments of a chromosome. In one implementation, a statistical value can include any average, mean, or median size of fragments of a chromosome. In another implementation, a statistical value can include a total length of fragments below a cutoff value, which may be divided by a total length of all fragments, or at least fragments below a larger cutoff value.

In step 140, a classification of whether a sequence imbalance (e.g. a fetal chromosomal aneuploidy) exists for the first location is determined based on the determined size distribution. In one embodiment, the ranking of a chromosome is compared to a reference ranking (e.g. one of a euploid sample). If the change is significant (e.g. exceeding a threshold), then the sample can be classified as aneuploid. In another embodiment, a statistical value of the actual sizes are compared between two chromosomes, or between groups of chromosomes. For example, a difference can be taken between the respective statistical values, and the difference compared to a cutoff.

II. Size Distribution (Rank)

Embodiments can use values of the size of nucleic acid fragments of a sample to determine if a chromosomal imbalance exists. The fragments are also called sequences after a sequencing has been performed. In one embodiment, a distribution of the size of fragments for a plurality of chromosomes is determined, and the chromosomes are ranked based on a statistical value (e.g. average, mean, or median) of the distribution. For convenience, the term "size" can be used herein synonymously with a statistical value of size. It should be clear when the term "size" is referring to the size of a specific fragment and a statistical measure of size of a set of fragments.

A. Rank

Figure 2:
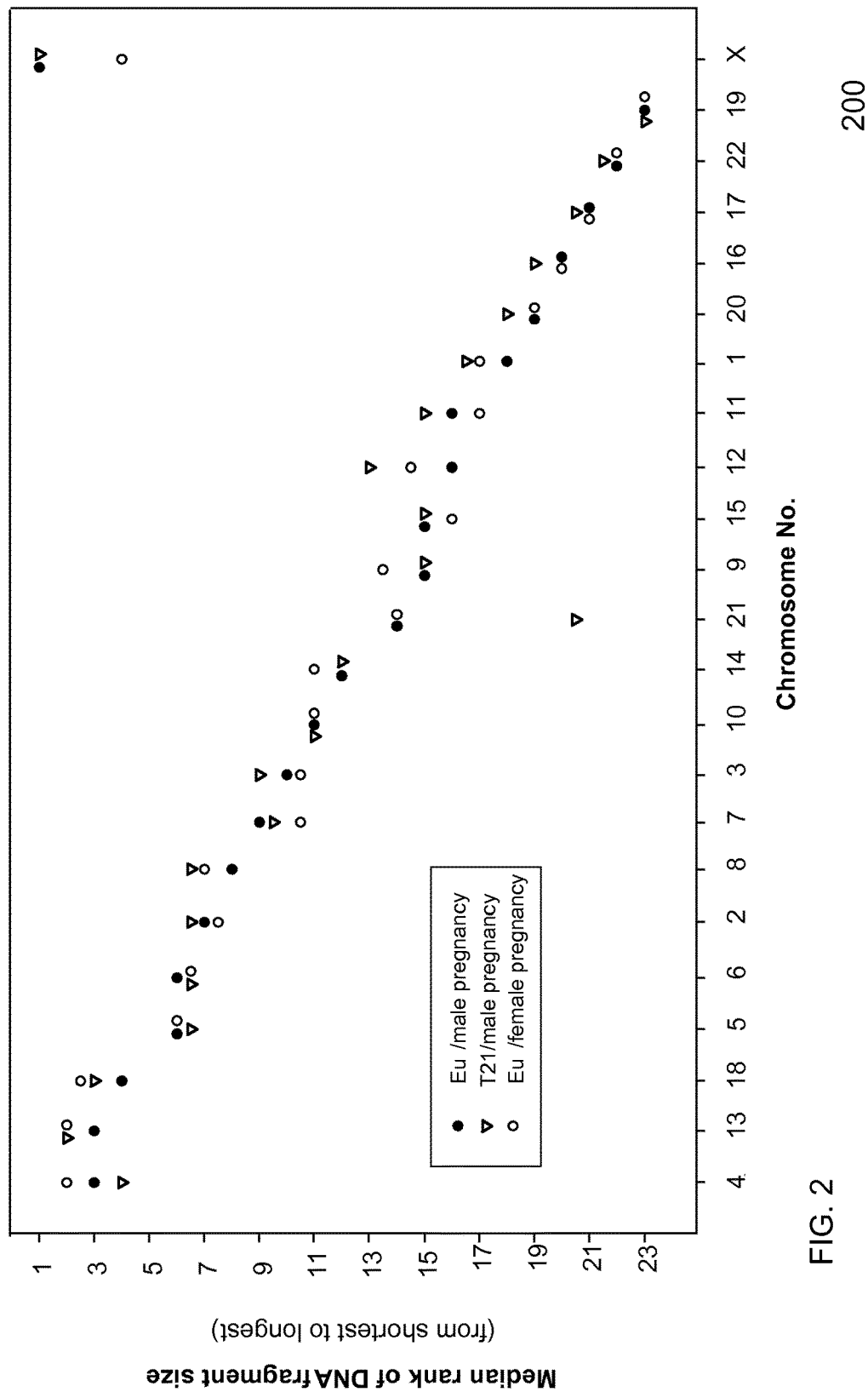
FIG. 2 is a plot showing median rankings of chromosomes in terms of the size of sequences aligned to it (when version 1 of the Illumina Cluster Generation Reagent Kit was used) according to embodiments of the present invention.

FIG. 2 is a plot 200 that illustrates the measured size distribution of the DNA fragments originated from different chromosomes in maternal plasma. As the measured size can reflect not just the DNA fragment size in vivo, but also the contribution of the analytical steps, it is expected that the size distribution might vary from platform to platform (e.g. for the Illumina Genome Analyzer and for the ABI SOLiD platform) and might even vary when different versions of reagents are used for a particular platform. However, as long as the reference samples and the test samples are analyzed using the same platform or reagent types, embodiments can be used in a platform/reagent-independent manner. Some embodiments may also be used with different platforms and/or reagent types, e.g., if any errors can be determined and corrected, or if the platforms and/or reagent types can be shown to have closely matched analytical performances.

In FIG. 2, the 22 autosomes and chromosome X were compared in terms of the size of fragment sequences aligned to them. On the Y-axis, the rank is in the descending order of the size of sequences, i.e. the chromosome with the longest sequences ranks 1 and the chromosome with the shortest sequences ranks 23. In one embodiment, the comparison (Kruskal-Wallis One Way Analysis of Variance on Ranks followed by Bonferroni-corrected pairwise comparisons) was made non-parametrically using the SigmaStat (SPSS) software. The comparison can be of any statistical value representing size, including a ranking of each of the individual sizes and a statistical analysis of the individual rankings for the sequences of each chromosome. In one implementation, ties and skips in the rank numbering are allowed.

In some embodiments, each of the sequences are mapped to a particular chromosome. Then, for each chromosome, one or more statistical values are determined for the sequences mapped to that chromosome. That is different types of statistical values (e.g. mean and median) can be calculated for the sizes of each chromosome. The corresponding statistical values can then be ranked. For example, the average sizes for each chromosome can be compared to each other. If more than one statistical value is used, then the statistical values can be combined (e.g. according to some formula, such as a weighted average), and this combined statistical value can be ranked. In one embodiment, the rankings of the statistical values for a particular chromosome can be combined (e.g. as mentioned above for the statistical values), and then the combined rankings can be compared to each other.

In other embodiments, all of the sequences are individually ranked according to size. That is if there are 1,000,000 sequences, then the rankings go from 1 to one million, with possible ties and skips in the rank numbering. The rankings for all sequences mapped to the same chromosome can then be added together. The sum of the rankings can be divided by the number of sequences aligned to the particular chromosome to arrive at the mean sequence ranking for the chromosome. The chromosome with the highest mean sequence ranking can be marked as the longest (ranks 1, highest on the Y-axis) and the chromosome with the lowest mean sequence ranking would be the shortest (ranks 23, lowest on the Y-axis). In another embodiment, a median rank can be determined. The median ranks of the cases with euploid male fetus, euploid female fetus and trisomy 21 male fetus are shown in FIG. 2.

On the X-axis, the chromosomes are arranged in a descending order of the size distribution of DNA fragments derived from each chromosome (with the exception of the X chromosome (see later)). In one embodiment, for such ranking, only the euploid cases were used. The chromosome with the longest measured size (e.g. length) is arranged on the left side. The X chromosome has been placed on the right of the diagram because its ranking is governed by the sex of the fetus.

As mentioned above, the measured size might vary from platform to platform (e.g., when one changes from the Illumina system to another system). Thus, in one aspect, the size can refer to the 'measured' size, as opposed to an actual size. The size might even change when one switches from one version of the Illumina kit to another one, e.g. when one changes from a version 1 paired-end cluster generation kit to version 2. In one embodiment, users can perform a ranking for their particular system.

It can be seen from FIG. 2 that the mean rank of the X chromosome is lower (i.e. becomes shorter) in the plasma of a pregnant woman carrying a female fetus, when compared with one carrying a male fetus. The explanation of this observation is that the DNA fragments released by a fetus are shorter than those from the mother. Thus, by releasing a double dose of the X chromosome, a female fetus will reduce the overall measured size fragments derived from the X chromosome in maternal plasma. Conversely, a male fetus would only be able to release a single dose of the X chromosome.

Also, one can see from FIG. 2 that the rank of chromosome 21 decreases (i.e. becomes shorter) in the plasma of a pregnant woman carrying a trisomy 21 fetus, when compared with one carrying a euploid fetus. The explanation of this observation can once again be traced back to the measured size fragments derived from chromosome 21 in maternal plasma. Conversely, a euploid fetus would only be able to release two doses of chromosome 21 per fetal cell.

Figure 3:
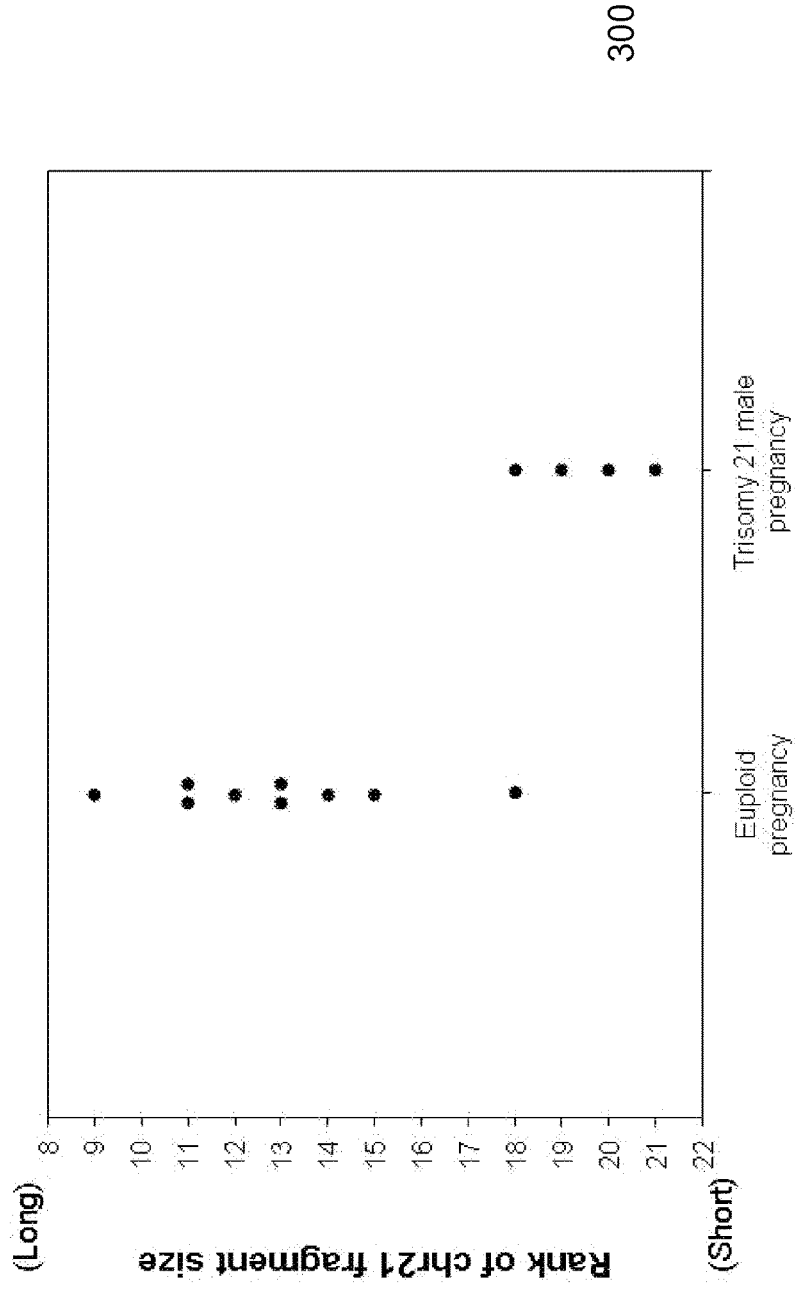
FIG. 3 is a graph demonstrating that a size analysis of sequences derived from different chromosomes in maternal plasma according to embodiments of the present invention can be used for the noninvasive prenatal detection of fetal chromosomal 21 aneuploidies

FIG. 3 is a graph 300 demonstrating that a size analysis of sequences derived from different chromosomes in maternal plasma according to embodiments of the present invention can be used for the noninvasive prenatal detection of fetal chromosome 21 aneuploidies. In this example, the chromosome size is represented by a size rank when compared with other chromosomes. Thus, a larger size rank number indicates that a chromosome has shorter DNA fragment sizes in maternal plasma.

Graph 300 demonstrates that the size rank number of chromosome 21 in maternal plasma is larger (thus indicating shorter DNA fragments) for pregnancies involving a trisomy 21 fetus (ranging from rank 18 to 21), than when the fetus is euploid (ranging from rank 9 to 18). The explanation of this observation is that fetal DNA is shorter than maternal DNA and that the additional dose of chromosome 21 from a trisomy 21 fetus would lead to an overall shortening of a statistical value of chromosome 21 sequences in maternal plasma.

B. Methods Using Rank

Figure 4:
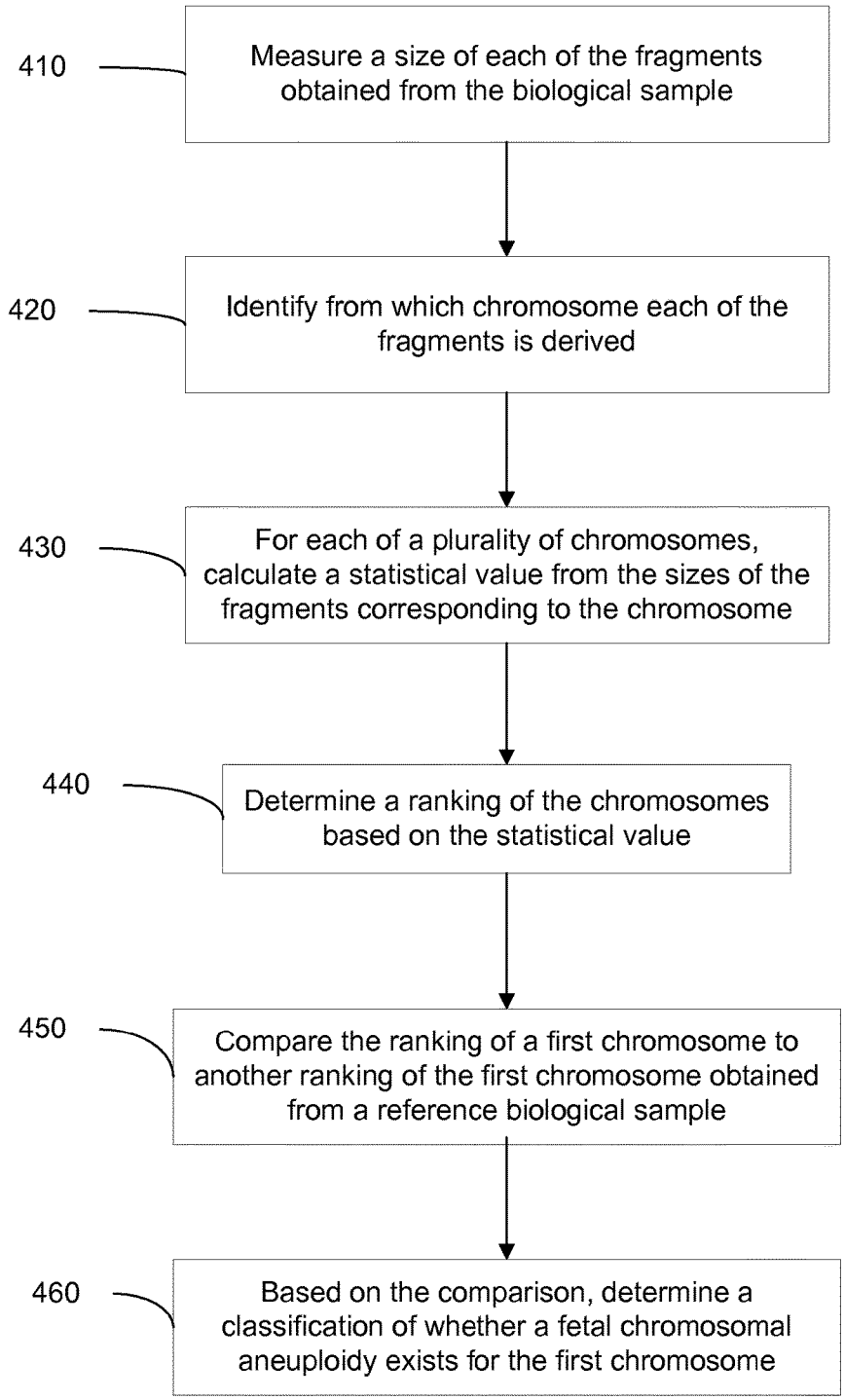
FIG. 4 is a flowchart illustrating a method of performing prenatal diagnosis of a fetal chromosomal aneuploidy in a biological sample obtained from a pregnant female subject using rankings of a statistical value of size according to embodiments of the present invention.

FIG. 4 is a flowchart illustrating a method of performing prenatal diagnosis of a fetal chromosomal aneuploidy in a biological sample obtained from a pregnant female subject using rankings of a statistical value of size according to embodiments of the present invention.

In step 410, a size of each of a plurality of nucleic acid molecules (fragments) obtained from the biological sample is measured. Note that this plurality of nucleic acid molecules may be a subset of all of the nucleic acid molecules obtained. The plurality of nucleic acid molecules may even be a subset of all the nucleic acid molecules that are sequenced, when sequencing is done as part of the size measurement.

In step 420, it is identified from which chromosome each of the plurality of nucleic acid molecules is derived. In various embodiments, the order of steps 410 and 420 can be reversed or occur simultaneously. For example, in the paired-end sequencing context, the genomic alignment of a sequence can provide its chromosomal location, plus its length (by subtraction of the start and end genomic coordinates). In one embodiment, the chromosome can be identified as in step 120.

In step 430, for each of a plurality of chromosomes, a statistical value is calculated from the sizes of nucleic acid molecules corresponding to the chromosome. The statistical value can be calculated in any of the ways described herein. For example, the statistical value could include a result of an initial ranking stage, as described above. In one embodiment, only a portion of the nucleic acid molecules corresponding to any particular chromosome may be used.

In step 440, a ranking of the chromosomes is determined based on the statistical values. In one embodiment, the ranking can be determined using a basic sorting algorithm. In another embodiment, more complicated comparison may be performed, such as a Kruskal-Wallis one way analysis of variance on ranks followed by Bonferroni-corrected pairwise comparisons, or other suitable methods. In various embodiments, the rankings could be integers, fractions, real numbers (e.g. in a range), or alphanumeric rankings based on a rubric (e.g. A-X).

In step 450, the determined ranking of a first chromosome is compared to another ranking of the first chromosome obtained from a reference biological sample. In one embodiment, the comparison is the comparison of the determined ranking against a cutoff threshold (e.g. a single value or range), which is determined from rankings of one or more reference biological samples. Such a cutoff value could be if the rank is 18 (or 19) or higher, as can be determined from FIG. 3. In another embodiment, a difference in the ranking of the first chromosome between the two samples can be determined, and the difference can be compared to a cutoff. In one implementation, the reference biological sample has been analyzed to determine that it does not contain the disease of interest, and it may even be determined that the sample does not contain any relevant disease that might cause problems with a ranking.

In step 460, based on the comparison, a classification of whether a fetal chromosomal aneuploidy exists for the first chromosome is determined. In one embodiment, the classification can be a binary classification of disease or not disease. In another embodiment, the classification can be ternary in that an indeterminate classification may be used. In yet another embodiment, the classification can include a probability of a particular classification, and thus effectively have more than just three classifications.

III. Size Distribution (Statistical Values of Size)

In other embodiments, the size distribution can include a statistical values of the size of the fragments (e.g. statistical values of the actual or absolute values for a particular genomic location), as opposed to the rankings. In one embodiment, actual sizes of a first chromosome can be compared to actual sizes of one or more reference chromosomes for a same test sample. For example, a separation value (e.g. a difference or ratio) between these actual sizes of the first chromosome and the one or more reference chromosomes can be compared to a cutoff. In one implementation, the cutoff can be determined from reference samples. In another embodiment, a separation value between the actual sizes of the fragments of a chromosome between a test sample and a reference biological sample might be used along with a cutoff. In yet another embodiment, the actual size of fragments of a chromosome might be compared against a cutoff to obtain a reliable classification.

A. Absolute Size

Some examples demonstrate that one can achieve the noninvasive prenatal detection of trisomy 21 by comparing the absolute sizes of fragments derived from chromosome 21 with those of fragments derived from one or more reference chromosomes. In one embodiment, chromosomes 7 and 14 can be selected as reference chromosomes, as they can have size values (e.g. absolute size or size rankings) in maternal plasma that are relatively close to chromosome 21. In practice, the reference chromosome may be any chromosome that has a fragment size that is consistent in its relation, e.g., on a specific analytical platform and/or reagent type, to chromosome 21 (or other chromosome of interest) for euploid samples.

FIG. 5 is a table 500 illustrating comparisons of chromosome 21 to chromosome 7 and chromosome 14 in terms of the size of sequences aligned to the respective chromosomes according to embodiments of the present invention. The data for table 500 is obtained from 16 test samples. For each sample, a mean size is shown for fragments of each of chromosomes 7, 14, and 21. A difference between the mean values is also provided. A p value shows a likelihood that each of the differences would occur in a healthy sample.

As can be seen from table 500 of FIG. 5, the sequences aligned to chromosome 21 were significantly shorter (e.g. by mean size) than the sequences aligned to chromosome 7 and chromosome 14 for all the trisomy 21 pregnancies (Mann-Whitney rank-sum test, p-value <0.001). Shortening at this degree of statistical significance was not observed in the euploid pregnancies. Thus, table 500 indicates that for all of the trisomy 21 pregnancies, the difference of the mean fragment size between chromosome 21 and chromosome 7 was greater than 1 bp whereas none of the euploid cases showed a difference more than 1 bp. Accordingly, 1 bp can provide an accurate cutoff for determining a classification. Similarly, for all of the trisomy 21 pregnancies, the mean fragment size from chromosome 14 is consistently larger than that of chromosome 21. Indeed, if a cutoff of 0.5 bp is used for the observed 'lengthening' of chromosome 14 fragments when compared with those from chromosome 21, all trisomy 21 cases can be distinguished from the non-trisomy 21 cases. Thus, in one embodiment, a cutoff value can be determined from one or more reference samples.

B. Methods Using Absolute Size

Figure 6:
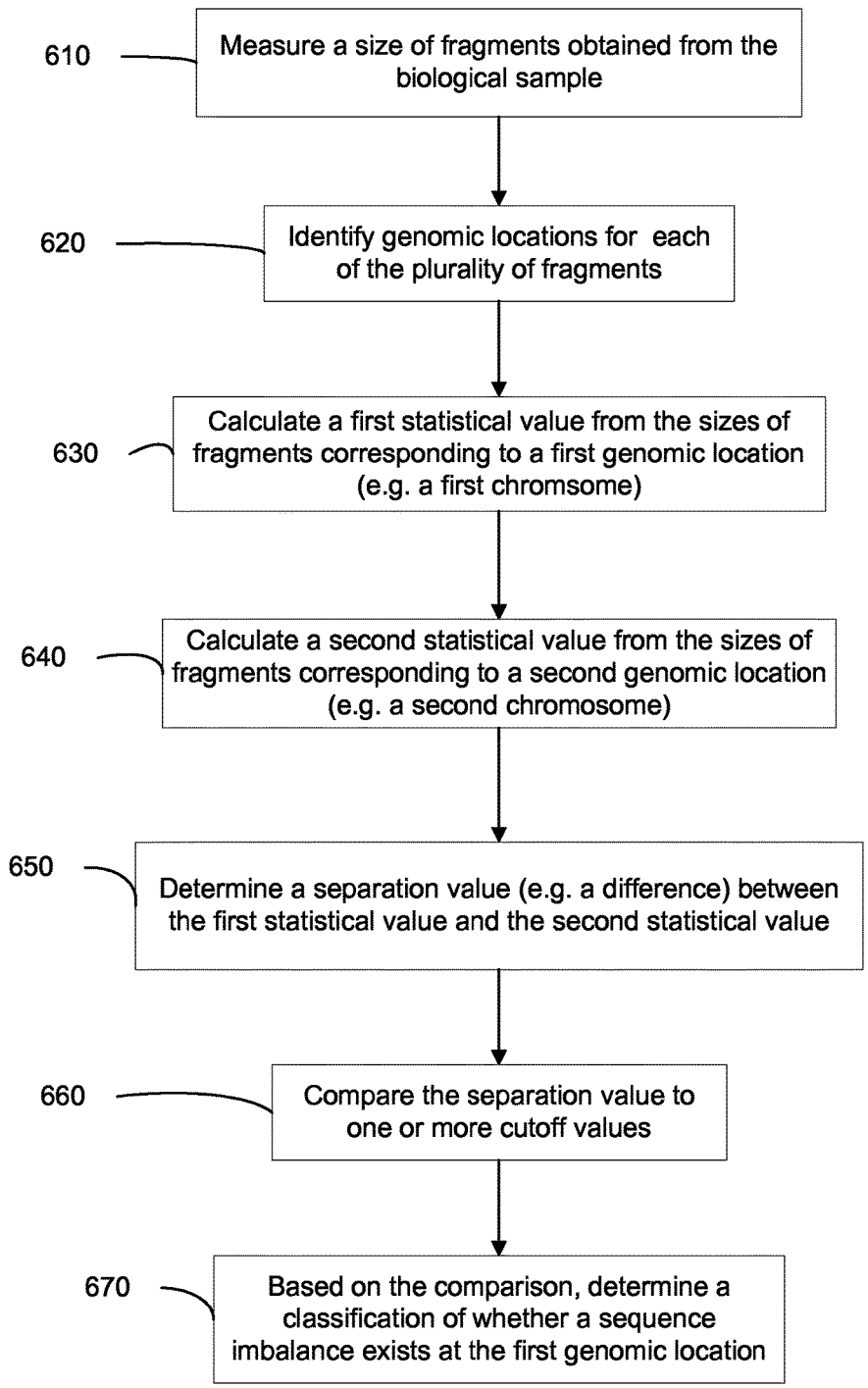
FIG. 6 is a flowchart illustrating a method of performing prenatal diagnosis of a sequence imbalance in a biological sample obtained from a pregnant female subject using a comparison of statistical value of a size of fragments for a genomic location according to embodiments of the present invention.

FIG. 6 is a flowchart illustrating a method of performing prenatal diagnosis of a sequence imbalance in a biological sample obtained from a pregnant female subject using a comparison of statistical value of a size of fragments for a genomic location according to embodiments of the present invention. In one aspect, method 600 can be directed to determining a classification of a sequence imbalance based on a separation value (e.g. a difference or ratio) for the size of fragments of a first chromosome and the size of fragments of one or more reference chromosomes.

In step 610, a size of a plurality of nucleic acid molecules obtained from the biological sample is measured. Note that the plurality of nucleic acid molecules may be obtained and include similar fragments as noted for step 410.

In step 620, a genomic location is identified from which each of the nucleic acid molecules is derived. The location can be any part of a genome, as is described for step 120 and elsewhere. For example, it is identified which chromosome each of the plurality of nucleic acid molecules is derived. This determination can be made by a mapping to a reference genome, as is described herein.

In step 630, a first statistical value is calculated from the sizes of the nucleic acid molecules corresponding to a first genomic location (e.g. a first chromosome). In one embodiment, the first statistical value can be an average, mean, or median size of the fragments corresponding to the first chromosome. In another embodiment, the first statistical value can include a sum of the length of fragments below a first size, which can be a type of cutoff. For example, each of the fragments that are smaller than 200 bp can have their lengths summed. The sum can be divided by another number, such as a sum of the lengths of all fragments corresponding to the first chromosome or a sum of the lengths of fragments greater than a second size cutoff (which may be the same as the first size). For example, the first statistical value can be a ratio of the total length of fragments below a first size cutoff relative to a total length of fragments, or a ratio of the total length of small fragments relative to a total length of large fragments.

In step 640, a second statistical value is calculated from the sizes of the nucleic acid molecules corresponding to a second genomic location (e.g. a second chromosome). The second chromosome can be considered a reference chromosome. In one embodiment, a statistical value for a plurality of reference chromosomes can be calculated. In one implementation, the statistical values can be combined such that the statistical value could be of one or more second chromosomes. In another embodiment, the statistical values for the plurality of reference chromosomes may be compared to individually, as mentioned below.

In step 650, the first statistical value and the second statistical are compared to obtain a separation value. In one embodiment, the separation value can be a difference between the first statistical value and the second statistical value is determined. In another embodiment, the separation value can be a ratio of the two statistical values. In yet another embodiment, a plurality of separation values can be determined, e.g., one for each second statistical value, which can be calculated for each reference chromosome.

In step 660, the separation value is compared to one or more cutoff values. In one embodiment, the comparison can be performed for each of a plurality of separation values. For example, as mentioned above, a different separation value can be determined between the first statistical value and each second separation value. In various implementations, each separation value can be compared to the same or different cutoff values. In another embodiment, a separation value is compared to two cutoff values to determine whether the separation value is within a particular range. The range can include one cutoff to determine if a non-normal data point occurs (e.g. an aneuploidy) and a second cutoff could be used to determine if the data point is likely caused by an error in measurement or analysis (e.g., if the separation value is larger than ever would be expected, even for a diseased sample).

In step 670, a classification of whether a sequence imbalance (e.g. a fetal chromosomal aneuploidy) exists for the first genomic location is determined based on the comparison. In one embodiment, a plurality of cutoffs (e.g. N cutoffs) can be used for a single separation value. In such an embodiment, N+1 classifications can be determined. For example, two cutoffs may be used to determine the classifications of euploid (normal or healthy), indeterminate, and aneuploid (diseased or unhealthy). In another embodiment where a plurality of comparisons are performed (e.g. one for each separation value), the classification can be based on each of the comparisons. For example, a rule based method can look at the classifications resulting from each of the comparisons. In one implementation, a definitive classification is only provided when all of the classifications are consistent. In another implementation, the majority classification is used. In yet another implementation, a more complicated formula may be used based on how close each of the separation values is to a respective cutoff value, and these closeness values can be analyzed to determine a classification. For example, the closeness values could be summed (along with other factors, such as a normalization) and the result could be compared to another cutoff value.

In other embodiments, variations of method 600 can also be applied to a direct comparison of a statistical value for the first chromosome to a cutoff value, which can be derived from a reference sample. Some embodiments can also be used for analyzing biological samples from non-pregnant individuals. Such an analysis can just look at a statistical value for a size of all of the fragments of a sample and compare the statistical value or a separation value to a cutoff to determine whether a sequence imbalance might exist. If an imbalance is classified as existing, further analysis of a location of the imbalance can be performed, e.g., by analyzing statistical size values and/or separation values for a particular genomic location (e.g. a chromosome).

C. Using Total Lengths of Short Fragments

As mentioned above, in some embodiments, the size distribution of the plasma DNA can also be reflected by the fraction of the total DNA length contributed by short DNA fragments. For example, the size distribution can include a total length of fragments below a cutoff value, which may be divided by a total length of all fragments, or at least fragments below a larger cutoff value. Conversely, the size distribution of the plasma DNA can also be reflected by the fraction of the total DNA length contributed by long DNA fragments. For example, the size distribution can include a total length of fragments above a cutoff value, which may be divided by a total length of all fragments, or at least fragments below a smaller cutoff value. As another example, a small vs. large ratio can also be used. One embodiment uses 150 bp as a cutoff to define short plasma DNA fragments. However, any cutoff, e.g. 130 bp, 140 bp, 160 bp and 170 bp, can also be used as cutoffs to define short DNA fragments. Note that as used herein, base pairs can also refer synonymously with a number of nucleotides (nt) in referring to a length of a single stranded fragment.

In one embodiment, a calculation of the fraction of DNA length contributed by short DNA fragments can be as follows: F=Fraction of DNA length contributed by short DNA fragments; S=Sum of the length of all short DNA fragments (length equal or below the cutoff); and T=Total length of all DNA fragments in the sample regardless of their length. The fraction can thus be provided by F=S/T, which is one example of a statistical value of size. A calculation of F may be for all fragments from a sample or for a particular location of the genome, e.g., for a particular chromosome.

In one implementation, the total length of all the DNA fragments in a sample can be determined. Then, a cutoff size (w) below which the DNA fragments are defined as "short fragments" can be selected. The cutoff size can be varied and be chosen to fit different diagnostic purposes. The total length of the short DNA fragments can be calculated by summing up the length of all DNA fragments that are equal to or shorter than the cutoff size. The fraction of total length contributed by short DNA fragments can be calculated as follows:

$$F = \Sigma^w \text{length}/\Sigma^{600}\text{length, where}$$

$\Sigma^w$ length represents sum of the lengths of DNA fragments with length equal to or less than cutoff w (bp); and $\Sigma^{600}$ length represents the sum of the length of DNA fragments equal to or less than 600 bp. The statistical value F can also be used in embodiments using ranking. For example, F can be calculated for fragments from each of a set of respective genomic locations (e.g. chromosomes).

For illustrative purpose, a total length was calculated by the summation of fragments shorter than 600 bp in the example below. However, other size limits, e.g. 400 bp, 500 bp and 700 bp, can be used for calculating the "total length". In this example, the total length was calculated based on DNA fragments of 600 bp or below because the Illumina Genome Analyzer (Solexa) system is not effective in amplifying and sequencing DNA fragments longer than 600 bp. In addition, limiting the analysis to DNA fragments of shorter than 600 bp can also avoid biases arising from structural variations of the genome. In the presence of structural variation, for example rearrangements (Kidd J M et al, Nature 2008; 453:56-64), the size of the DNA fragment can be overestimated when the size is estimated bioinformatically by mapping the ends of the DNA fragment to the reference genome. In addition, >99.9% of all the DNA fragments successfully sequenced and mapped to the reference genome are less than 600 bp and, thus, including all fragments equal to and shorter than 600 bp would provide a representative estimation of the size distribution of the DNA fragments in the sample.

As discussed above, a shift to a shorter size distribution for DNA fragments can be observed for a chromosome which the fetus has an extra copy. In one aspect, the measurement of the difference in the fractions of total length contributed by short DNA fragments between the chromosome at risk for the aneuploidy (target chromosome) and chromosomes not being at risk for aneuploidy (reference chromosomes) can be a quantitative measurement to determine if the size distributions for DNA fragments derived from these chromosomes are different.

In one embodiment, we define $F_{(Tar)}$ and $F_{(Ref)}$ as the fractions of total length contributed by short DNA fragments for the chromosome at risk of the aneuploidy and the reference chromosome(s), respectively. The difference in the fractions of total length contributed by short DNA fragments between the target chromosome and the reference chromosome(s) ($\Delta F_{(Tar-Ref)}$) can be calculated as: $\Delta F_{(Tar-Ref)} = F_{(Tar)} - F_{(Ref)}$. For instance, $\Delta F_{(21-1)}$ is the difference between the fractions of total length contributed by short DNA fragments for chromosome 21 and chromosome 1. The application of $\Delta F_{(Tar-Ref)}$ in the prenatal diagnosis of fetal chromosomal aneuploidies will be discussed in the following sections. In another embodiment, a ratio of $F_{(Tar)}/F_{(Ref)}$ can also be used as a separation value in a similar manner as $\Delta F_{(Tar-Ref)}$ is used.

A difference between the F values of the target and the reference chromosomes can be used as a statistical value to determine if the fetus is trisomic for the target chromosome or not. When the fetus is trisomic for the target chromosome, the trisomic chromosome of the fetus would contribute an additional dosage of short fetal DNA to the maternal plasma, hence, resulting in an apparent shortening of the size distribution of the target chromosome sequences. This shortening of the size distribution of the target chromosome sequences would lead to an increase in the fraction of sequence length contributed by the short DNA fragments for the target sequence ($F_{target}$). As a result, there would be an increase in the difference $\Delta F$ between $F_{target}$ and $F_{ref}$.

Figure 7:
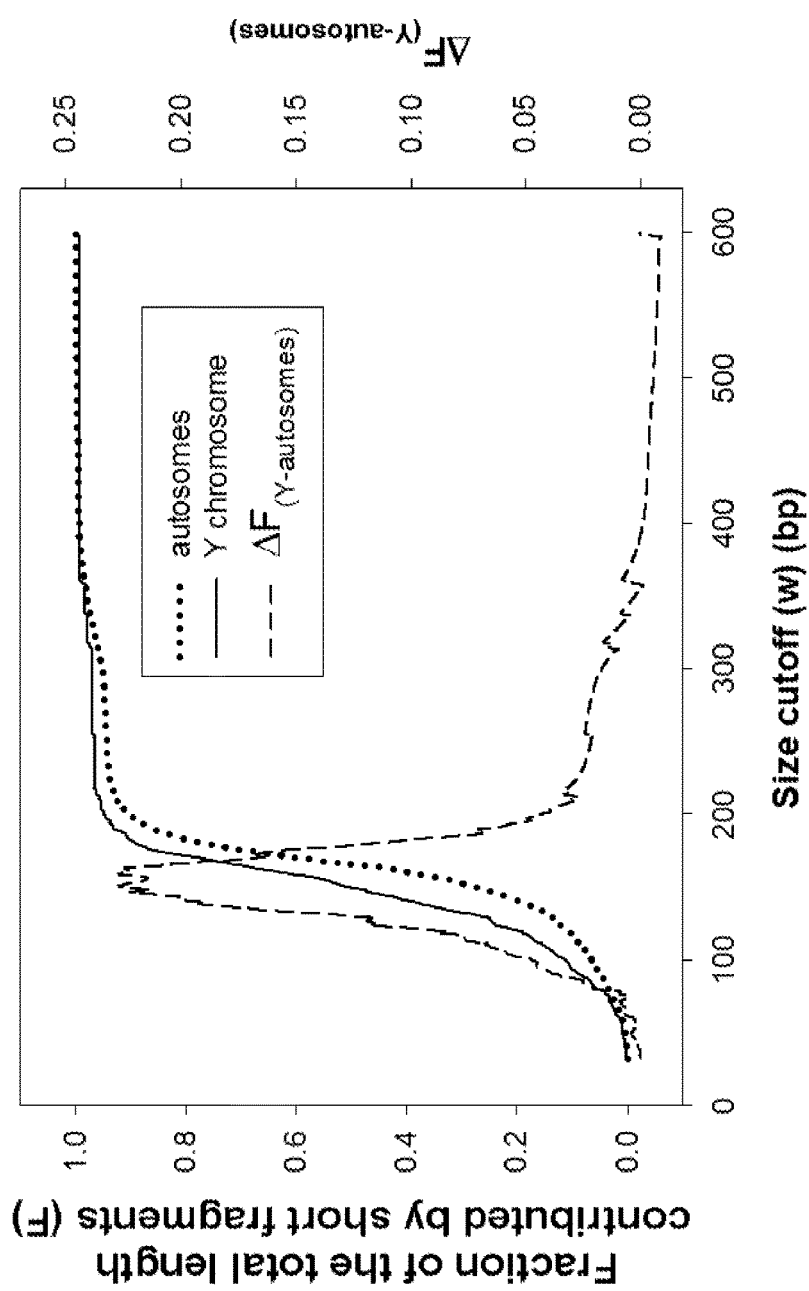
FIG. 7 shows a plot 700 of the fraction of total length contributed by short fragments (F) against the cutoff size (w) according to embodiments of the present invention.

FIG. 7 shows a plot 700 of the fraction of total length contributed by short fragments (F) against the cutoff size (w) for a maternal plasma sample with a male fetus. The F values for the DNA fragments aligned to the autosomes and chromosome Y are plotted on the vertical axis against the cutoff size used for defining "short DNA fragments". In male pregnancies, the DNA molecules aligned to chromosome Y represent the DNA released from the male fetus. As most of the circulating DNA molecules in maternal plasma are derived from the mother, the DNA fragments aligned to the autosomes should represent predominantly the maternal DNA fragments. The F value increases with the cutoff size and approaches the value of 1.0 when all DNA fragments in the sample are shorter than or equal to the cutoff size. The difference in size distribution between two species of DNA molecules can be reflected by the difference in their F values. A higher F value indicates that a higher fraction of the total length is contributed by the short fragments and, thus, indicates a shorter size distribution of the DNA fragments.

As shown in plot 700, the size distribution for DNA molecules from chromosome Y is shorter than the size distribution of DNA from the autosomes. Specifically, the F value for chromosome Y rises earlier than that for the autosomes, resulting in a higher $F_Y$ than $F_{autosomes}$ between 80 bp to 350 bp. The difference in the F values between chromosome Y and the autosomes ($\Delta F_{(Y-autosomes)}$) is further plotted against the cutoff size and is represented by a dashed line, which is positive between 80 bp to 350 bp. The maximum value for $\Delta F_{(Y-autosomes)}$ is 0.23 occurring at around 150 bp. As illustrated in the following examples, the difference in the fraction of the total fragment length contributed by the short fragments ($\Delta F$) between the at-risk chromosome and the reference chromosome(s) is a useful separation value to quantify the difference in their size distributions. Further by way of example, one could determine the $\Delta F$ value with any size cutoff, e.g., one between 130 bp and 170 bp.

Figure 8:
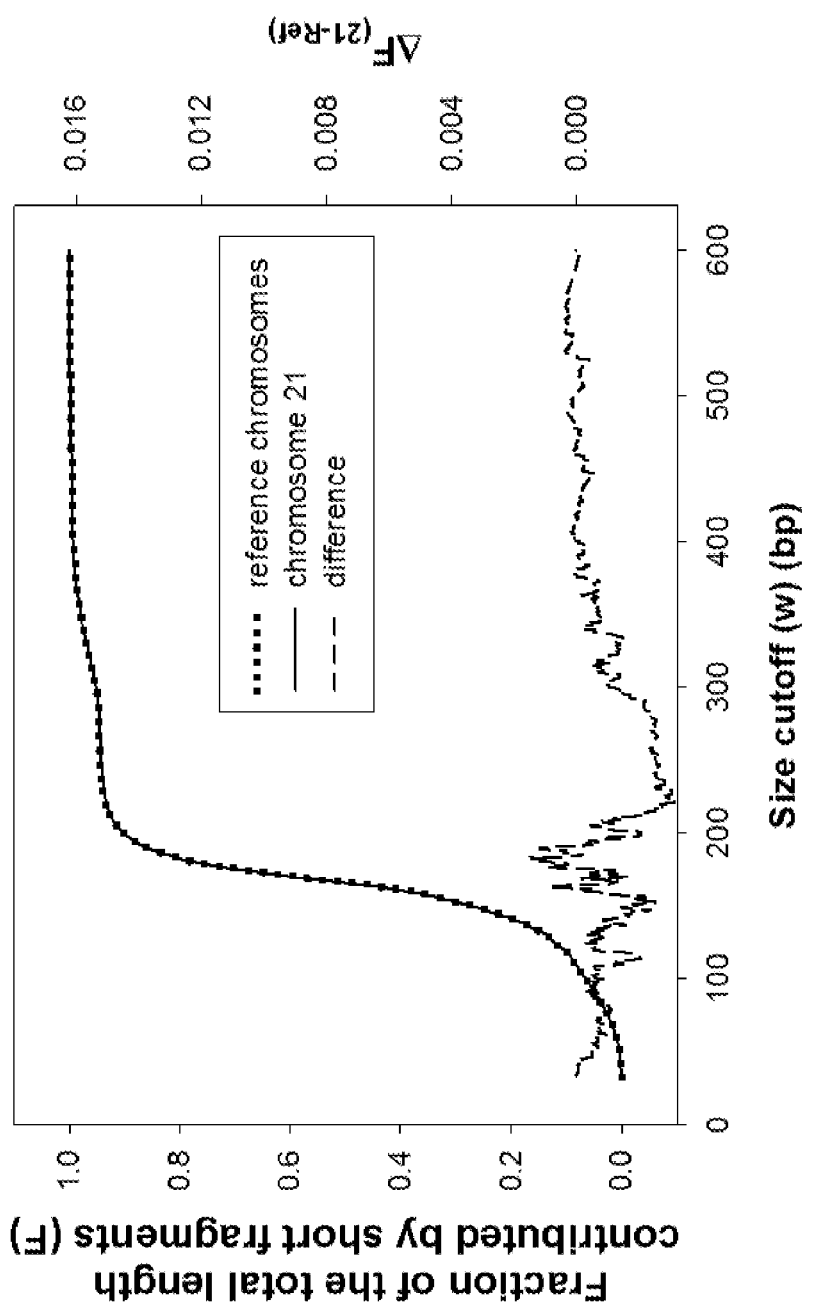
FIG. 8 shows a plot 800 of the fraction of total length contributed by short fragments (F) for chromosome 21 (solid line) and the reference chromosomes (all autosomes except chromosomes 13, 18 and 21) (dotted line) against the cutoff size for a euploid pregnancy according to embodiments of the present invention.

FIG. 8 shows a plot 800 of the fraction of total length contributed by short fragments (F) for chromosome 21 (solid line) and the reference chromosomes (all autosomes except chromosomes 13, 18 and 21) (dotted line) against the cutoff size for a euploid pregnancy. The difference in the two F values ($\Delta F_{(21-Ref)} = F_{(chr12)} - F_{(Ref)}$) is represented by the dashed line. As the size distributions of DNA fragments from chromosome 21 and the reference chromosomes are similar in a euploid pregnancy, the value of $\Delta F_{(21-Ref)}$ is close to zero for any cutoff size.

Figure 9:
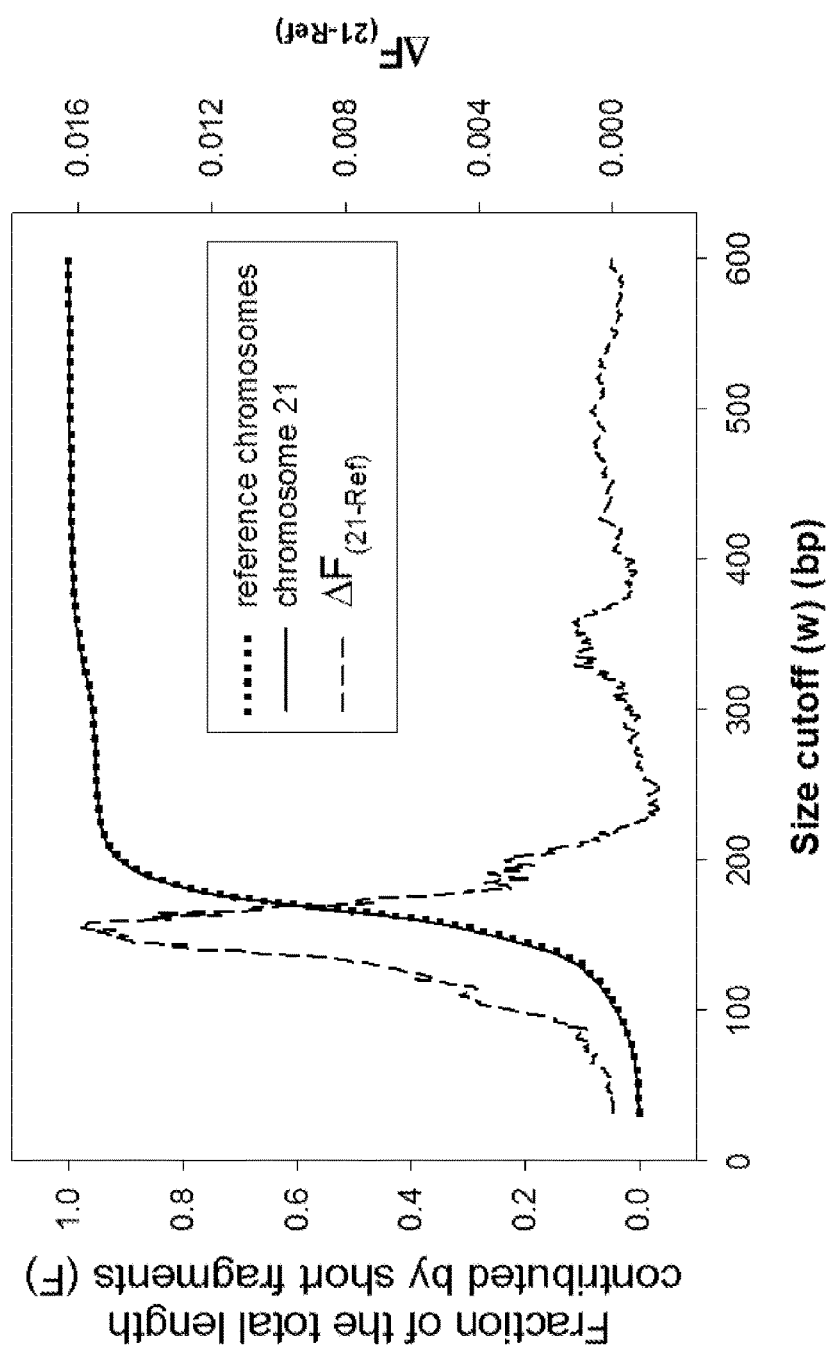
FIG. 9 shows a plot 900 of the F values for chromosome 21 (solid line) and the reference chromosomes (all autosomes except chromosomes 13, 18 and 21) (dotted line) against the cutoff size for a trisomy 21 pregnancy according to embodiments of the present invention.

FIG. 9 shows a plot 900 of the F values for chromosome 21 (solid line) and the reference chromosomes (all autosomes except chromosomes 13, 18 and 21) (dotted line) against the cutoff size for a trisomy 21 pregnancy. The $\Delta F_{(21-Ref)}$ is represented by the dashed line. Due to the additional dosage of chromosome 21 from the fetus, the size distribution of DNA fragments in maternal plasma for chromosome 21 is shorter than that for the reference chromosomes. This difference in the size distributions of DNA fragments is reflected by the positive value of $\Delta F_{(21-Ref)}/$ which reaches a maximum of 0.016 at approximately 150 bp.

Figure 10:
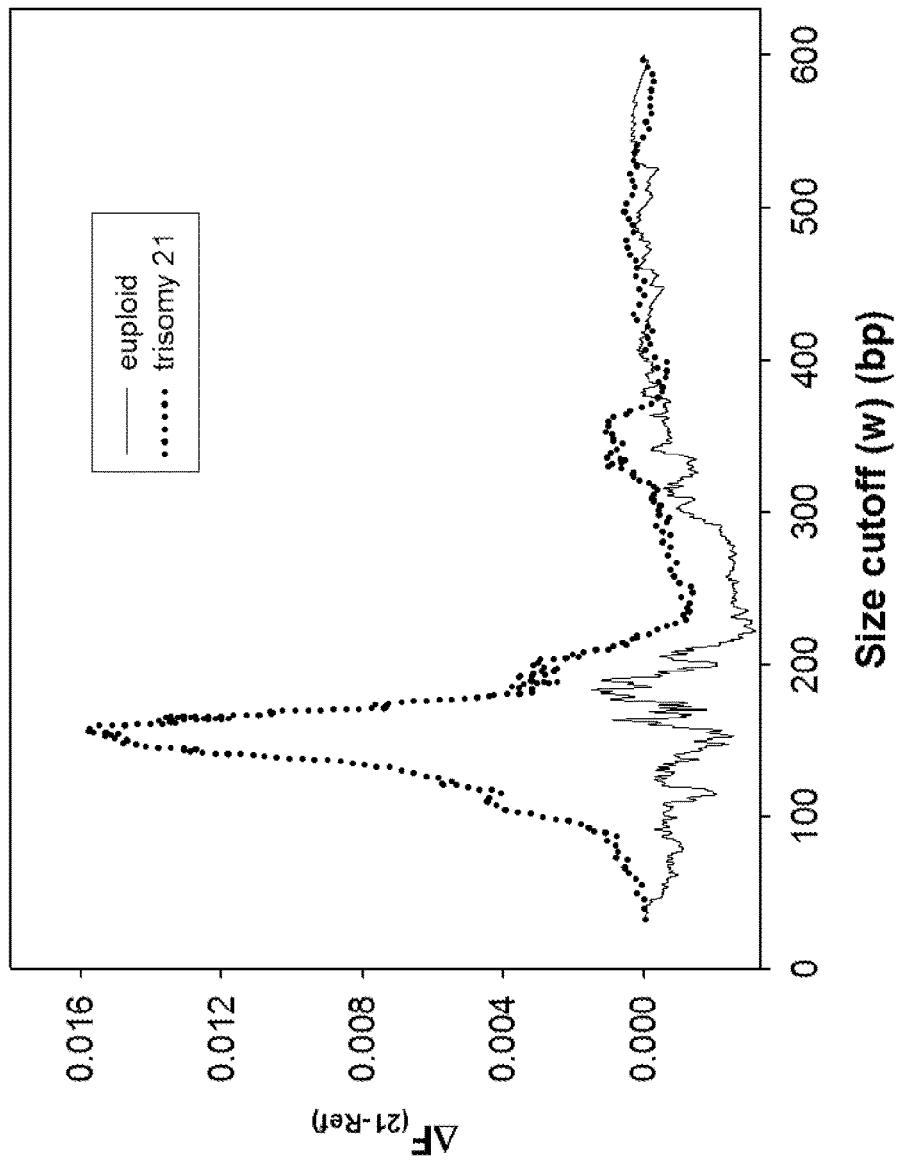
FIG. 10 shows a plot 1000 of $\Delta F_{(21-Ref)}$ between chromosome 21 and the reference chromosomes (all autosomes except chromosomes 13, 18 and 21) against the size cutoff for a euploid and a trisomy 21 pregnancy according to embodiments of the present invention.

FIG. 10 shows a plot 1000 of $\Delta F_{(21-Ref)}$ between chromosome 21 and the reference chromosomes (all autosomes except chromosomes 13, 18 and 21) against the size cutoff for a euploid and a trisomy 21 pregnancy. An increased $\Delta F_{(21-Ref)}$ is observed in the trisomy 21 case but the $\Delta F_{(21-Ref)}$ is approximately zero at each size cutoff for the euploid case. As the maximum $\Delta F_{(21-Ref)}$ is observed at around 150 bp, the difference at 150 bp can be used as a separation value for determining if there is any significant shortening of the size distribution of the chromosome 21 sequences. However, any size at which a significant difference between euploid and trisomic cases arises can be used, for example, but not limited to 140 bp, 145 bp, 155 bp and 160 bp. In this example, the difference in the fraction of the total length of chromosome 21 and the reference chromosomes observed at 150 bp are 0.016 and −0.002 for the trisomy 21 and euploid pregnancies, respectively.

This difference in the shape of the fraction of the total DNA length contributed by short DNA fragments can be used to distinguish between a euploid and an aneuploid fetus. A difference can be tested in various ways. In one embodiment, the value of ΔF at a particular size cutoff (an example of a separation value) can be compared to a cutoff value to determine a categorization (classification) of a sample. In another embodiment, a peak value in ΔF can be found and that value can be compared to one or more categorization cutoff values. In various embodiments, a peak value can be a maximum or minimum value, an average value near a max/min value, or other value associated with or derived from a max/min value). Other statistical values of a separation value (e.g ΔF) for can also be used, such as the width of the peak, or a location of the particular size cutoff corresponding to the peak.

In one embodiment, an F value (or other statistical value described herein, such as length of small fragments divided by length of large fragments) obtained from a plurality of fragments for a particular genomic location or for the entire genome can be used to determine if a pathology exists. For example, if the statistical value exceeds a cutoff value, then a pathology can be identified as existing since the amount of small fragments is outside of a normal range. This could be done for patients besides a pregnant female to identify diseases other than those of a fetus.

In some embodiments, a physical size fractionation can be performed prior to a size analysis of fragments. In one embodiment, the nucleic acid molecules can be separated into two size fractions (e.g. one larger than 200 bp, and one less than or equal to 200 bp), and then a size distribution of selected chromosomes (e.g. chromosome 21) on each of these size fractions can be compared. In the presence of a fetal trisomy (e.g. trisomy 21), the size fraction of smaller molecular size would increase in relative abundance compared with the size fraction of larger molecular size.

In other embodiments, a number of fragments below a length cutoff value can be used instead of a size distribution. For example, the number of fragments below a length cutoff value can be compared (e.g. a difference or ratio) for the target chromosome (e.g. chromosome 21) relative to one or more reference chromosomes. In one embodiment, the number of fragments below the length cutoff value is divided by the total number of fragments to obtain a percentage, and this percentage can be compared between the target chromosome and the one or more reference chromosomes to provide a parameter. The resulting parameter (e.g. difference or ratio) can be compared to a cutoff value (e.g. 1%). In one aspect, the length cutoff may be chosen at a length where the above percentage is the highest.

V. Examples Using Rank

In addition to trisomy 21, fragment size analysis in maternal plasma can also be used for the noninvasive prenatal detection of other fetal chromosomal aneuploidies, such as trisomy 13, trisomy 18 and sex chromosome aneuploidies (such as Turner syndrome, Klinefelter syndrome and XYY, etc). Embodiments can also be used when the chromosomal abnormality involves only a portion of a particular chromosome (e.g. trisomy 21 caused by chromosomal translocation). In such a scenario, fragment size abnormalities will be observed for DNA fragments from the affected chromosomal regions.

FIG. 11 shows a table 1100 for libraries of maternal plasma DNA that were constructed using a multiplexing sample preparation kit (Illumina) according to the manufacturer's instructions. Every two samples with distinguishable barcodes were introduced into one lane and subsequently subjected to standard multiplexed paired-end sequencing on an Illumina Genome Analyzer II. The samples could be distinguished on the basis of barcodes. The plasma samples of 120 pregnant women were analyzed. The sex and the chromosomal aneuploidy status of the fetuses are shown in Table 1100.

Figure 12:
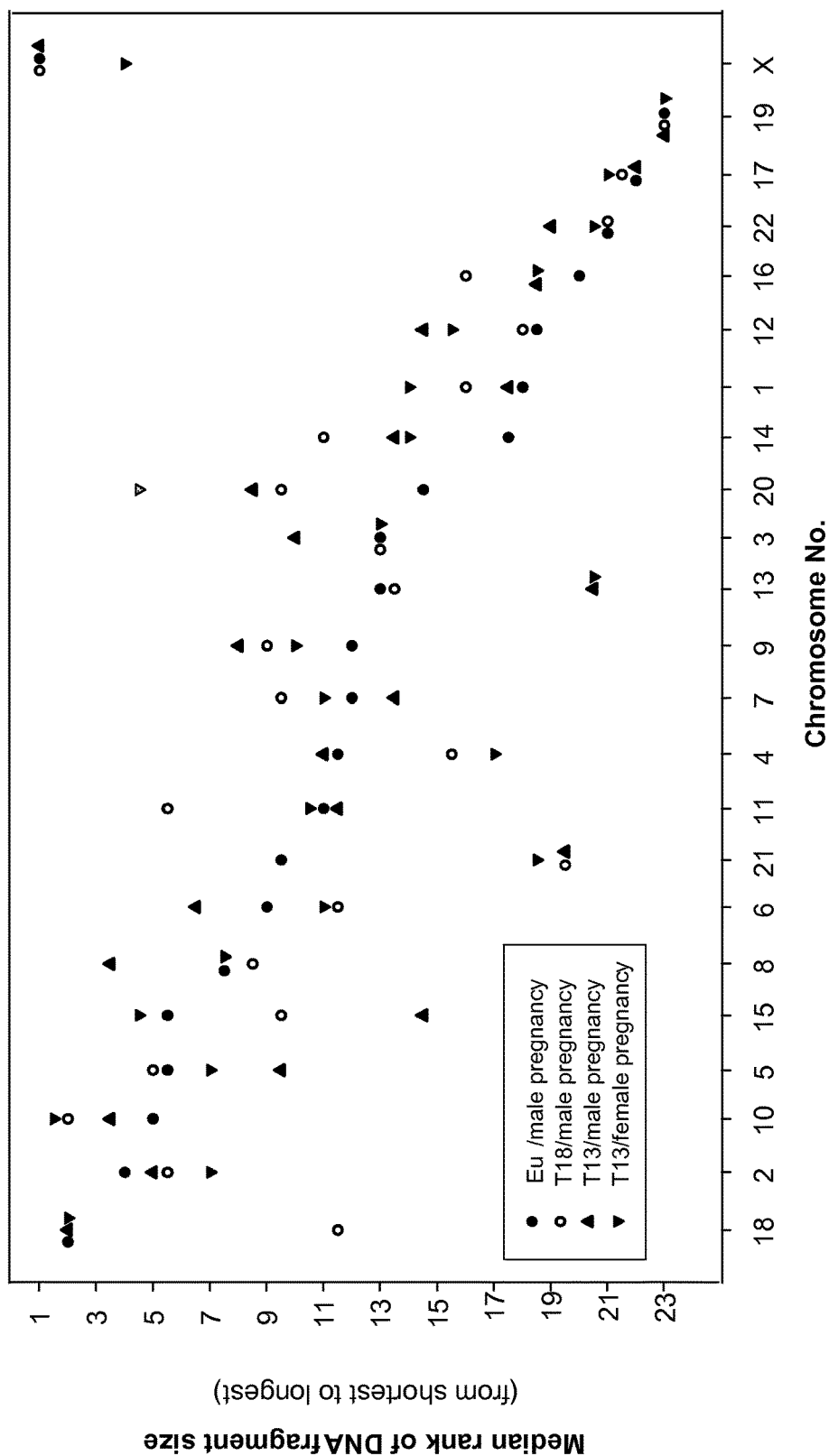
FIG. 12 illustrates the ranking of the different chromosomes for four samples of different disease or non-disease states according to embodiments of the present invention.

FIG. 12 illustrates the ranking of the different chromosomes for four samples of different disease or non-disease states according to embodiments of the present invention. The 22 autosomes, together with chromosome X, were ranked according to the size of their fragments as described earlier. As can be seen, the relative ranking of the chromosomes based on version 2 of the Illumina Cluster Generation Reagent Kit is different from when version 1 of the kit was used (FIG. 2). As shown below, embodiments (e.g. method 400) allow an aneuploid case to be differentiated from a euploid case.

A. Trisomy 13

Figure 13:
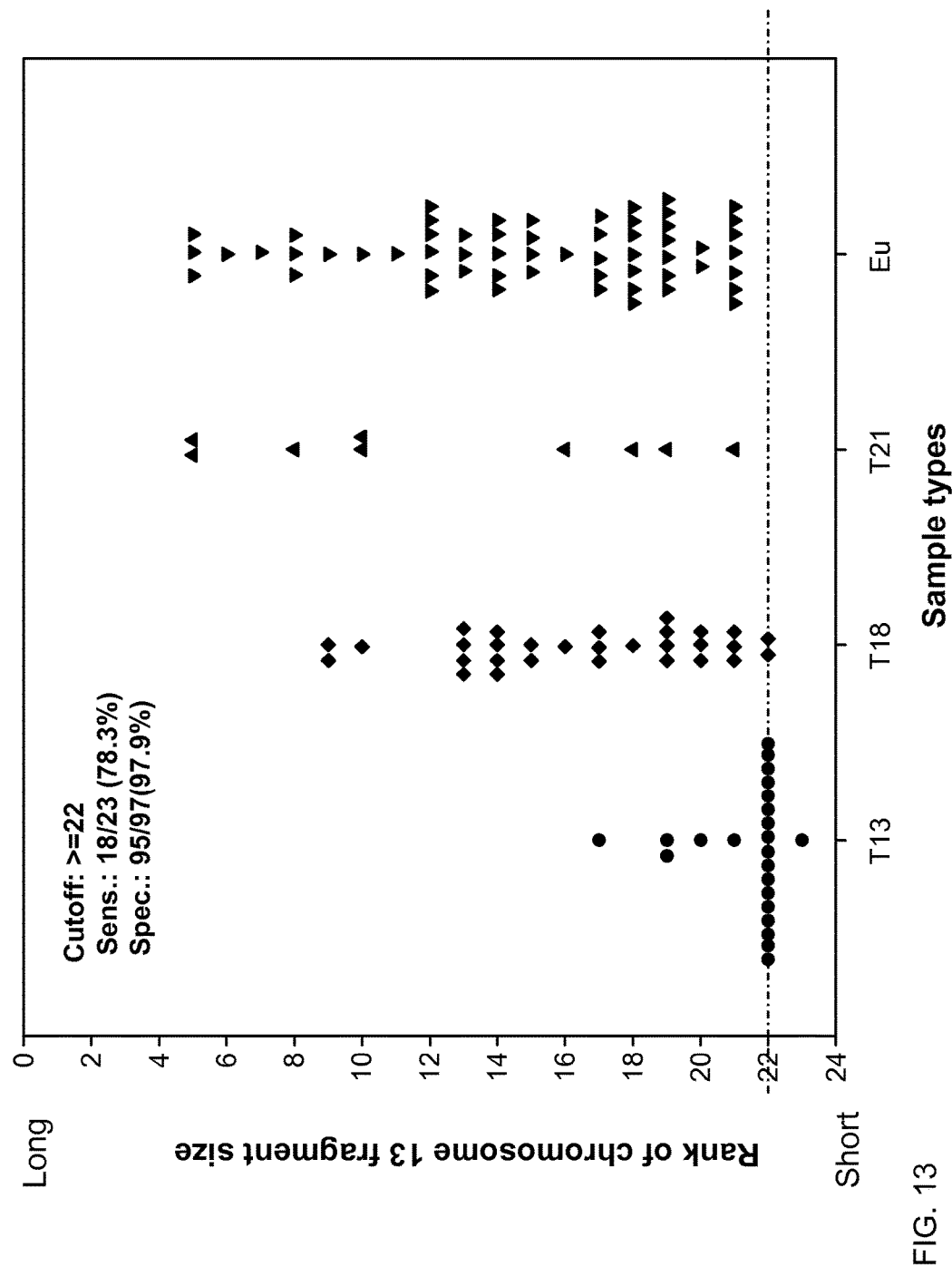
FIG. 13 shows a ranking of chromosome 13 for the 120 cases of euploid, trisomy 13, trisomy 18, and trisomy 21 according to embodiments of the present invention.

In this example, we demonstrate the use of embodiments for the prenatal diagnosis of trisomy 13. FIG. 13 shows a graph of the rank of chromosome 13 for the 120 pregnancies, e.g., as may result from method 400. In the graph, T13, T18, T21 and Eu refer to trisomy 13, trisomy 18, trisomy 21 and euploid pregnancies, respectively. In 18 (78.3%) of the 23 trisomy 13 pregnancies, chromosome 13 ranked 22 or below whereas in only 2 (2.1%) of the 97 non-trisomy 13 pregnancies, chromosome 13 ranked 22 or below. Therefore, using a cutoff ranking of 22, the sensitivity and specificity of rank analysis of chromosome fragment size for prenatal diagnosis of fetal trisomy 13 were 78.3% and 97.9%, respectively.

In FIG. 13, one can see that the rank of chromosome 13 was higher (i.e. with a smaller number denoting the rank) for euploid and trisomy 18 and 21 pregnancies than for trisomy 13 pregnancies. In other words, when compared with sequences on the other chromosomes, the chromosome 13 sequences appear to be shorter for the trisomy 13 pregnancies than for the non-trisomy 13 pregnancies. The apparent shortening of chromosome 13 sequences in trisomy 13 pregnancies is due to the increased contribution of fetal DNA to chromosome 13 due to the extra chromosome 13 of the fetus.

B. Trisomy 18

Figure 14:
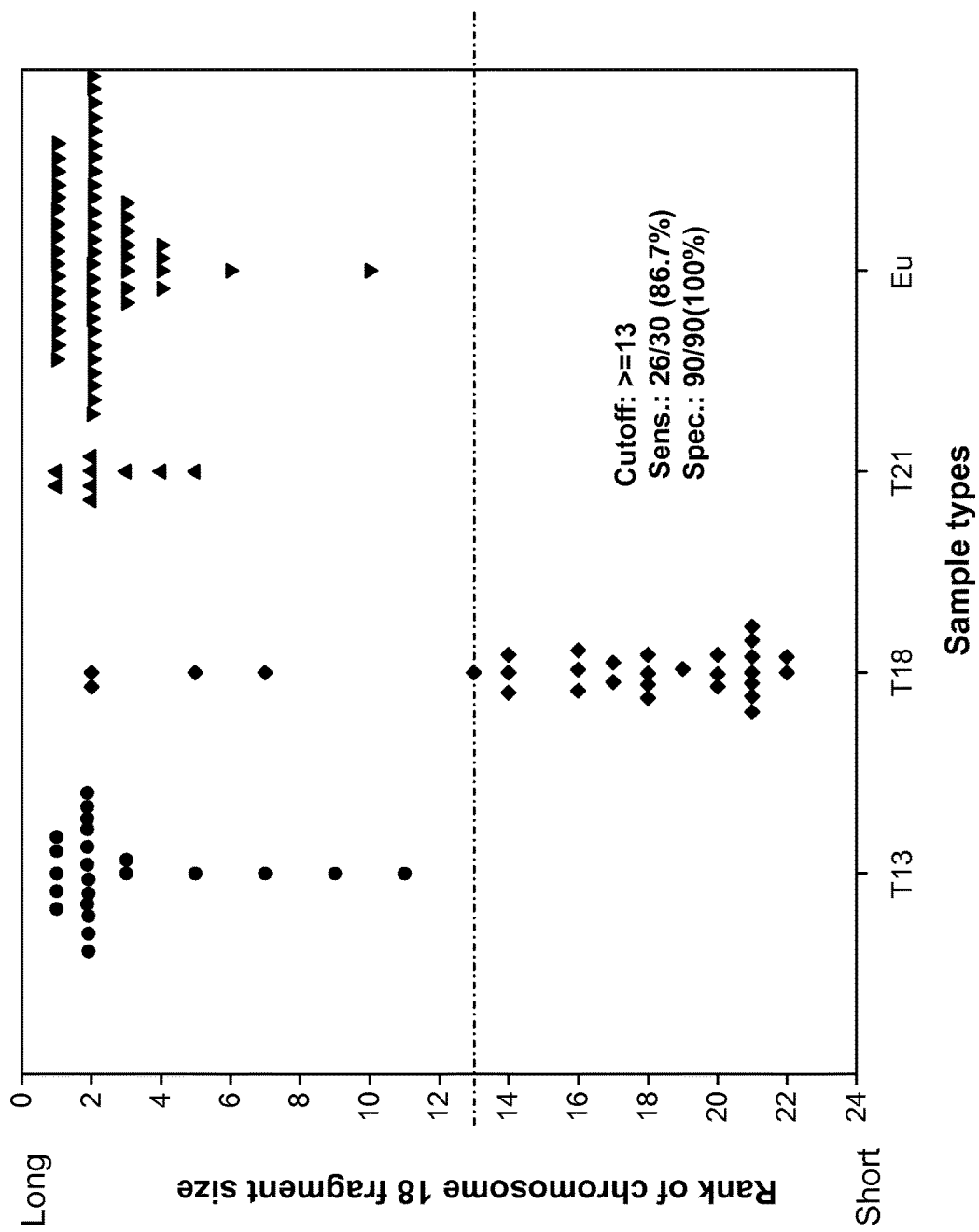
FIG. 14 shows a ranking of chromosome 18 for the 120 cases of euploid, trisomy 13, trisomy 18, and trisomy 21 according to embodiments of the present invention.

FIG. 14 shows a ranking of chromosome 18 for the 120 cases. In 26 (86.7%) of the trisomy 18 cases, the ranks of chromosome 18 were lower (i.e. with a large number denoting the rank) than 13 whereas none of the 90 non-trisomy 18 cases had a rank lower than 13. Therefore, using a rank of 13 as a cutoff, the sensitivity and specificity of ranking analysis of chromosome fragment size for the prenatal diagnosis of fetal trisomy 18 are 86.7% and 100%, respectively.

In this analysis, we have compared the size ranking of chromosome 18 in trisomy 18, trisomy 13, trisomy 21, and euploid pregnancies. In the context of chromosome 18, the latter three groups can both be regarded as 'normal' controls because they do not have dosage abnormalities involving chromosome 18. As can be seen from FIG. 14, the rank for chromosome 18 for euploid and trisomy 13 cases are clustered around 1 to 3. On the other hand, the ranks for chromosome 18 for the trisomy 18 cases are 13 to 22, indicating that the size of chromosome 18 fragments is shorter than that in the euploid, trisomy 21, and trisomy 13 cases. Again, the extra chromosome 18 explains these observations.

C. Trisomy 21

Figure 15:
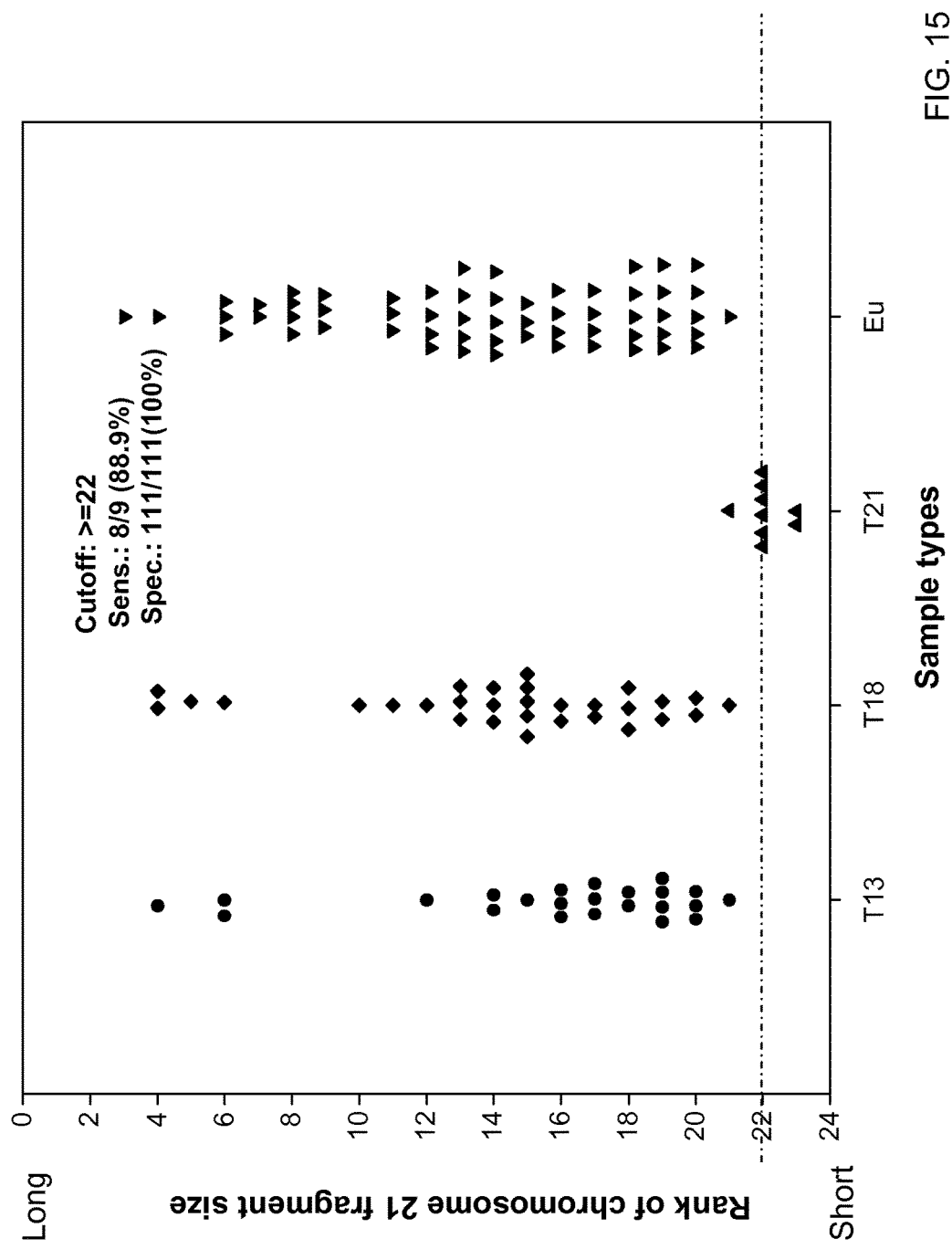
FIG. 15 shows a ranking of chromosome 21 for the 120 cases of euploid, trisomy 13, trisomy 18, and trisomy 21 according to embodiments of the present invention.

FIG. 15 shows a ranking of chromosome 21 for the 120 cases. In 8 (88.9%) of the 9 trisomy 21 cases, chromosome 21 ranked 22 or lower whereas in none of the 111 non-trisomy 21 cases, chromosome 21 had a rank of 22 or lower. Therefore, using a rank of 22 as a cutoff, the sensitivity and specificity of ranking analysis of chromosome fragment size for the prenatal diagnosis of fetal trisomy 21 would be 88.9% and 100%, respectively.

V. Examples Using Difference in Size

A. Trisomy 13

In these next examples, we demonstrate that one can achieve the noninvasive prenatal detection of trisomy 13 by comparing the absolute sizes of fragments derived from chromosome 13, with those of fragments derived from one or more reference chromosomes, e.g. as described for method 600. This example utilizes the same dataset as that in the previous example. As an illustration, for trisomy 13 detection, we have selected chromosome 5 and chromosome 6 as reference chromosomes.

As can be seen from table 1600 of FIG. 16, within the same sample, the sequences aligned to chromosome 13 were significantly shorter than the sequences aligned to chromosome 5 and chromosome 6 for all the trisomy 13 pregnancies (Mann-Whitney rank-sum test, p-value ≤0.001). As controls, euploid and trisomy 18 pregnancies were included. In both euploid and trisomy 18 pregnancies, the dosage of chromosome 13 was normal. As can be seen from table 1600, size abnormalities of such statistical significance for chromosome 13-derived sequences were not seen in euploid and trisomy 18 pregnancies.

Furthermore, for all the trisomy 13 pregnancies, within the same sample, the difference of the mean fragment size between chromosome 13 and chromosome 5 was greater than 0.4 bp whereas none of the non-trisomy 13 cases showed a difference more than 0.4 bp. Similarly, for all the trisomy 13 pregnancies, the difference of the mean fragment size between chromosome 13 and chromosome 6 was greater than 0.5 bp whereas none of the non-trisomy 13 cases showed a difference more than 0.5 bp.

B. Trisomy 18

As an illustration, for trisomy 18 detection, chromosome 14 has been selected as the reference chromosome. For non-trisomy 18 pregnancies, it can be seen in table 1700 of FIG. 17 that sequences derived from chromosome 18 are statistically significantly longer than those derived from chromosome 14 (Mann-Whitney rank-sum test, p-value ≤0.005). However, for the trisomy 18 cases, the chromosome 18 sequences were not significantly longer than sequences aligned to chromosome 14. The euploid and trisomy 18 cases can be differentiated based on the difference between the mean size of DNA fragment from chromosomes 18 and 14 using a cutoff value of 0 bp. These observations can be explained by the fact that the additional dose of fetal-derived chromosome 18 sequences which are shorter than maternal ones would reduce the overall size of such sequences when the fetus has trisomy 18. This would then bring the overall size distribution of chromosome 18 closer to the distribution of chromosome 14.

V. Examples Using Total Length Contribution

In the examples below, the reference chromosomes consisted of all the autosomes except chromosomes 13, 18 and 21.

Figure 18:
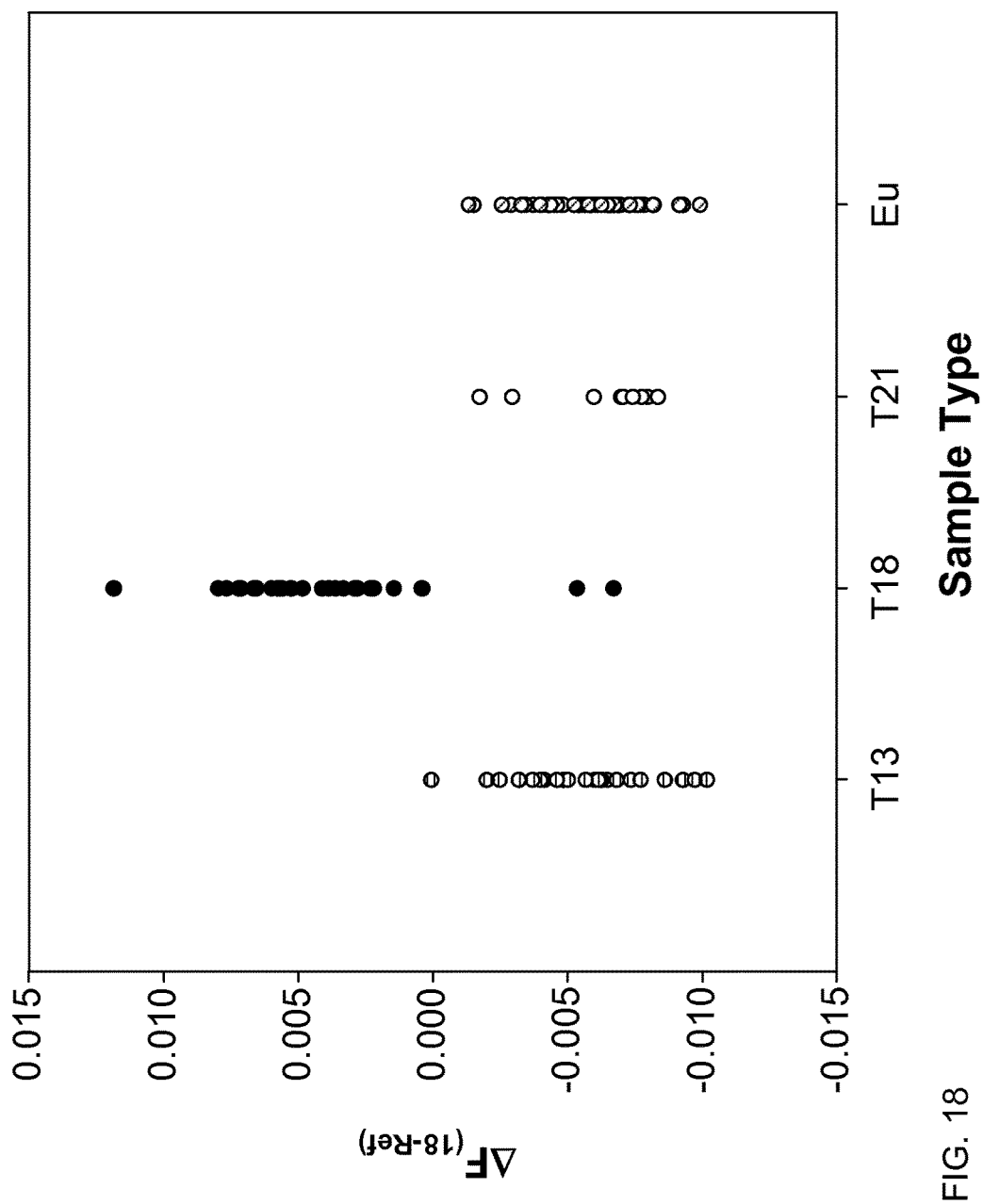
FIG. 18 shows a difference in the fractions of the total length contributed by short fragments between chromosome 18 and the reference chromosomes ($\Delta F_{(18-Ref)}$) at 150 bp according to embodiments of the present invention.

FIG. 18 shows a difference in the fractions of the total length contributed by short fragments between chromosome 18 and the reference chromosomes ($\Delta F_{(18-Ref)}$) at 150 bp. Using a diagnostic cutoff value of 0.0003 for $\Delta F_{(21-Ref)}$, the trisomy 18 pregnancies can be detected with 93.3% sensitivity and 100% specificity.

Figure 19:
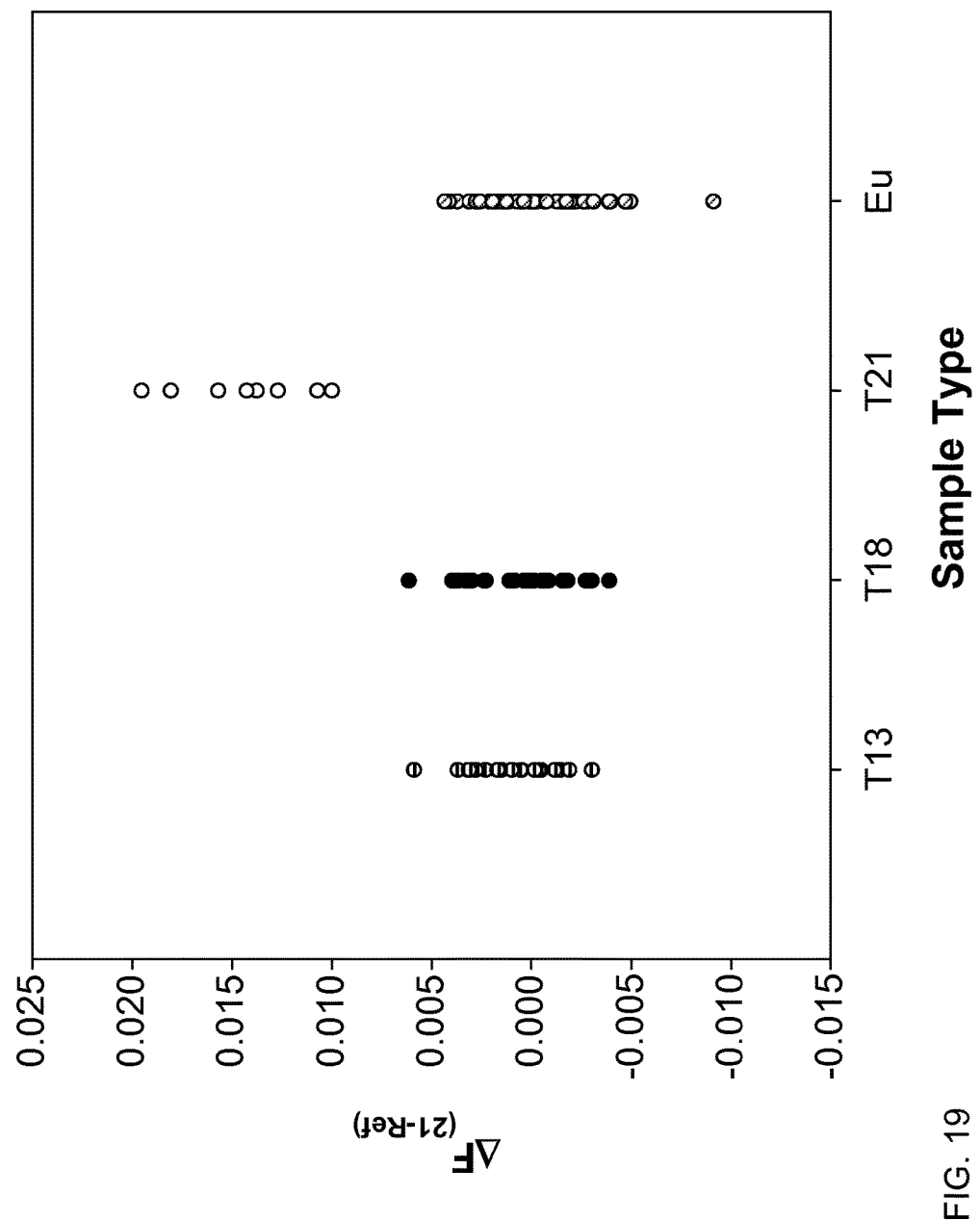
FIG. 19 shows a difference in the fractions of the total length contributed by short fragments between chromosome 21 and the reference chromosomes ($\Delta F_{(21-Ref)}$) at 150 bp according to embodiments of the present invention.

FIG. 19 shows a difference in the fractions of the total length contributed by short fragments between chromosome 21 and the reference chromosomes ($\Delta F_{(21-Ref)}$) at 150 bp. Using a diagnostic cutoff value of 0.007 for $\Delta F_{(21-Ref)}$, the trisomy 21 pregnancies can be detected with 100% sensitivity and 100% specificity.

VII. Selection of Reference Chromosome(S)

One or more reference chromosomes can be selected in various ways for the noninvasive prenatal detection of fetal chromosome aneuploidy by size analysis of maternal plasma DNA, e.g. using method 600. In various embodiments, different reference chromosomes can be selected.

A first type of reference chromosomes are those in which DNA fragments derived from them exhibit a similar size distribution on a specific analytical platform (or analytical platforms with closely matched analytical performances) as those derived from the chromosome potentially involved in an aneuploidy in maternal plasma (e.g. chromosome 21, 18, or 13). In one embodiment, in this type of analysis, a fetal chromosomal aneuploidy is detected if the size ranking or absolute size of the at-risk chromosome shows a statistically significant reduction from the reference chromosome(s). In other embodiments, one can measure the mean or median size difference between fragments derived from the at-risk chromosome and those from the reference chromosome(s).

A second type of reference chromosomes are those in which DNA fragments derived from them are statistically shorter than those derived from the chromosome potentially involved in an aneuploidy in maternal plasma (e.g. chromosome 21, 18, or 13) when the fetus is euploid. This type of scenarios may be encountered when the at-risk chromosome is one of the longest when measured using a particular platform. For example in FIG. 12, chromosome 18-derived DNA fragments were the longest amongst the autosomes when measured in maternal plasma. Thus, one can select reference chromosomes whose fragments are statistically significantly shorter than chromosome 18. In one embodiment, in this type of analysis, a fetal chromosomal aneuploidy is detected in a case if the size ranking or absolute size of the at-risk chromosome cannot be seen to be statistically significantly different from the reference chromosome(s). For example, this strategy has been used for the analysis for FIG. 17, as described above.

A third type of reference chromosomes are those in which DNA fragments derived from them are statistically longer than those derived from the chromosome potentially involved in an aneuploidy in maternal plasma (e.g. chromosome 21, 18, or 13) when the fetus is euploid. This type of scenarios may be encountered when the at-risk chromosome is one of the shortest when measured using a particular platform. Thus, one can select reference chromosomes whose fragments are statistically significantly longer than the at-risk chromosome. In one embodiment, in this type of analysis, a fetal chromosomal aneuploidy is detected in a case if the size ranking, difference in ranking or absolute size between the reference and the at-risk chromosome is increased.

A fourth type of reference chromosomes are those with similar GC content. The GC content of a chromosome can affect the quantitative readout in a sequencing reaction. One way to minimize potential bias resulting from a difference in GC content between chromosomes is to select appropriate reference chromosomes with similar GC content. FIG. 20 shows a list of the GC contents of different chromosomes (NCBI build 36, version 48). The chromosomes are listed in ascending order of the GC content. An example of using reference chromosomes with similar GC content is now provided.

Figure 21:
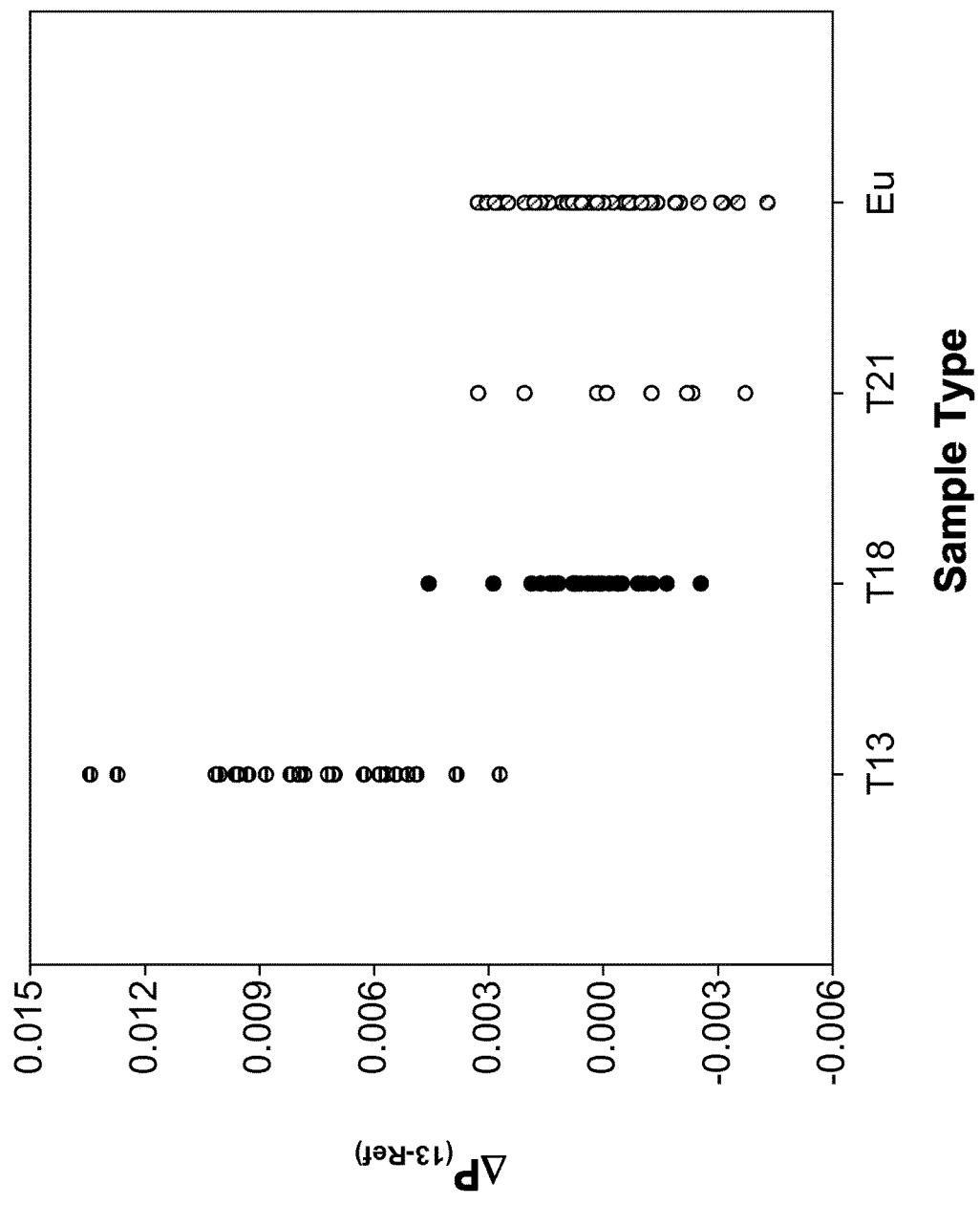
FIG. 21 shows a difference in the fractions of the total length contributed by short fragments between chromosome 13 and the reference chromosomes ($\Delta F_{(18-Ref)}$) at 150 bp according to embodiments of the present invention.

FIG. 21 shows a difference in the fractions of the total length contributed by short fragments between chromosome 13 and the reference chromosomes ($\Delta F_{(13-Ref)}$) at 150 bp. Here, by way of illustration, we used chromosomes 3, 4, 5 and 6 as the reference chromosomes for the $\Delta F_{(13-Ref)}$ analysis. As shown in FIG. 20, chromosomes 3-6 have GC content of 36.53%-38.79%, which is similar to GC content of 37.10% for chromosome 13. Using a diagnostic cutoff of 0.0038, the $\Delta F$ analysis detected trisomy 13 cases with a sensitivity of 95.7% and a specificity of 99.0%.

It is expected that the GC bias issue may affect different sequencing platforms to different extents. For example, the use of platforms which do not require prior amplification, such as the Helicos platform (Harris T D, et al. Single-molecule DNA sequencing of a viral genome. Science 2008; 320:106-9), nanopore (Lund J, Parviz B A. Scanning probe and nanopore DNA sequencing: core techniques and possibilities. Methods Mol Biol 2009; 578:113-22), or the single molecule real time system from Pacific Biosciences (Eid J, et al. Real-time DNA sequencing from single polymerase molecules. Science 2009; 323:133-8), might allow a broader choice of the reference group of chromosomes.

IV. Use of Fetal DNA Concentration

In trisomy 21 (or other trisomy) pregnancies, the fetus will release an extra dose of chromosome 21 fragments, which would be shorter than those from maternal cells, into maternal plasma. One would expect that the concentration of these shorter fragments will be correlated with the concentration of fetal DNA in maternal plasma. In other words, the higher the fractional concentration of Y chromosome-derived sequences, the shorter will be the measured size of chromosome 21-derived sequences in trisomy 21 pregnancies.

Figure 22:
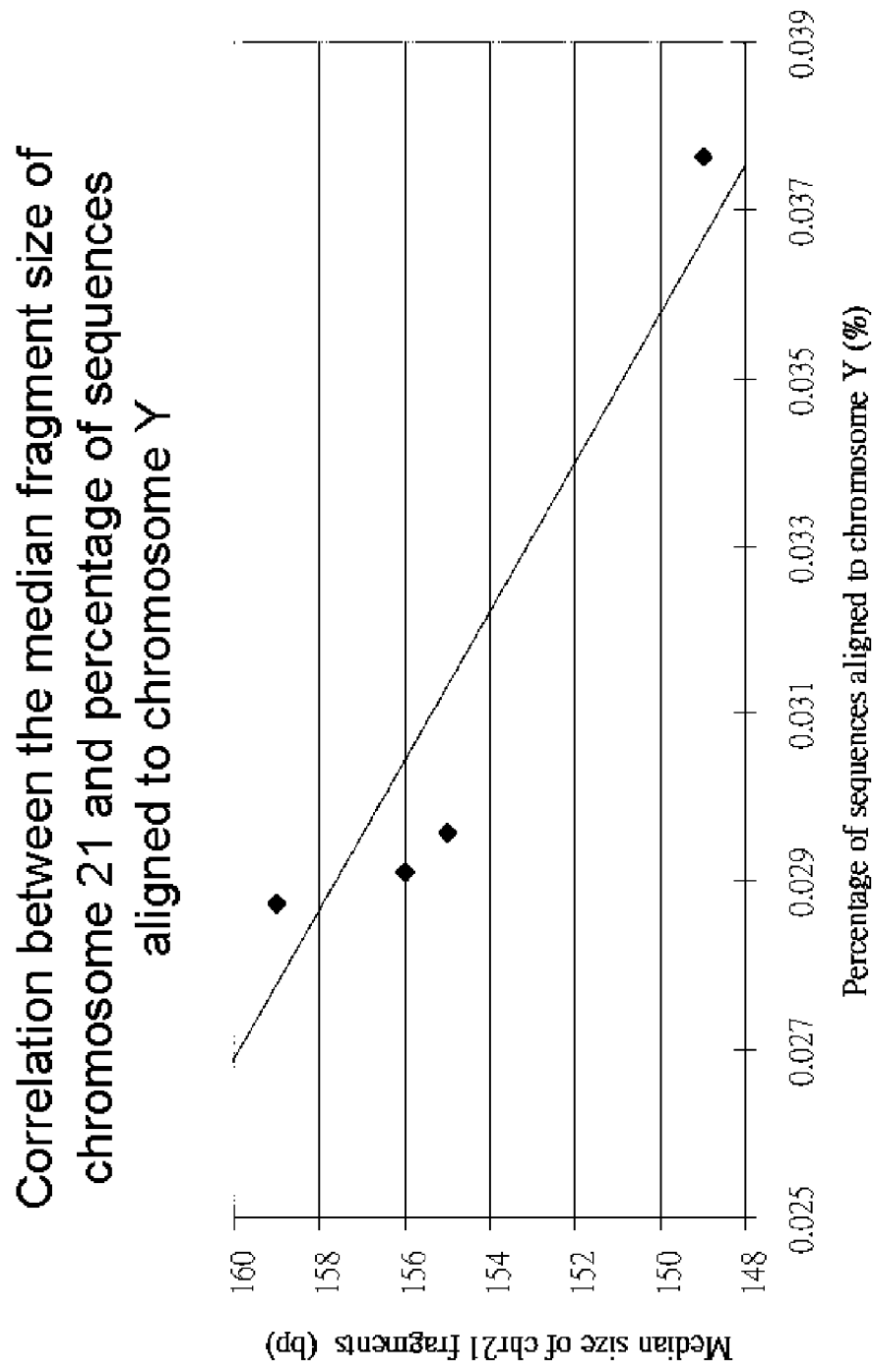
FIG. 22 is a plot showing correlation between the median size of sequences aligned to chromosome 21 and percentage of sequences aligned to the Y-chromosome according to embodiments of the present invention.

FIG. 22 illustrates the results from a number of pregnancies involving male trisomy 21 fetuses. As can be seen in FIG. 22, there is indeed a negative correlation between the median size of chromosome 21 sequences and the percentage of sequences aligned to the Y chromosome (r=−0.942, Pearson correlation). A similar trend would also be expected if the size ranking of chromosome 21 is used, i.e., the rank number of chromosome 21 will increase, indicating shorter fragments when the fractional fetal DNA concentration is increased. As there is a correlation, embodiments can use a measurement of fetal DNA concentration as a parameter in any of the methods described herein.

In this type of analysis, the fractional and absolute concentration of fetal DNA in maternal plasma can be measured by any method known to those skilled in the art. If the fetus is male, the concentration of fetal DNA can be measured by the fractional concentration of sequences derived from the Y chromosome in maternal plasma. Another example is the use of paternally-inherited genetic markers such as single nucleotide polymorphisms or simple tandem repeat polymorphisms or insertion-deletion polymorphisms. Another example is the use of epigenetic markers such as regions that are differentially methylated between fetal and maternal DNA (Poon et al. Clin Chem 2002; 48: 35-41; Chiu et al. Am J Pathol 2007; 170: 941-950; Chan et al. Clin Chem 2006: 52: 2211-2218; U.S. Pat. No. 6,927,028). The above markers can be analyzed using methods known to those of skill in the art, including polymerase chain reaction (PCR), digital PCR, sequencing, massively parallel sequencing and targeted massively parallel sequencing.

In one embodiment, one could vary the diagnostic threshold (e.g. cutoff value for any method described herein) for detecting a chromosomal aneuploidy in relation to the measured fetal DNA concentration in maternal plasma. Thus, for maternal plasma samples with a relatively high fetal DNA, the degree of shortening of plasma DNA molecules derived from the chromosome potentially involved in the aneuploidy would be expected to be more dramatic than for maternal plasma samples with a relatively low fetal DNA concentration.

Figure 23A:
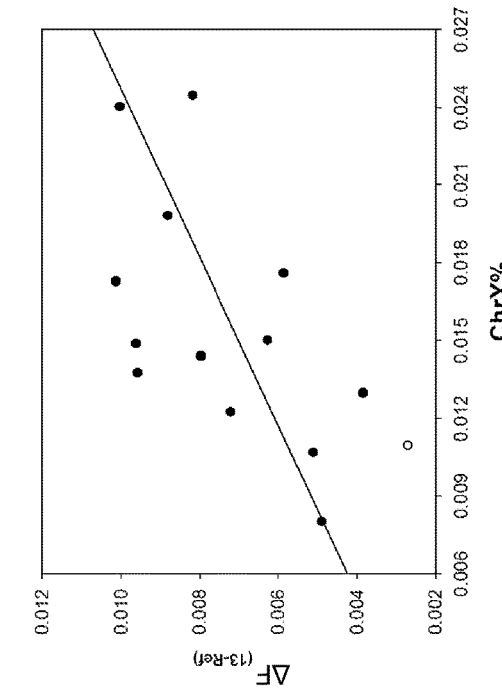
FIG. 23A-23C are plots showing correlation between the median size of sequences respectively aligned to chromosomes 18, 13, and 21 and percentage of sequences aligned to the Y-chromosome according to embodiments of the present invention.

As $\Delta F$ is related to the size distribution, $\Delta F$ also shows a correlation with fetal DNA concentration. FIG. 23A shows a correlation between $\Delta F_{(18-Ref)}$ (chromosome 18 vs. reference chromosomes) and fetal DNA concentration. Ten of the thirty T18 cases were carrying male fetuses, and thus the fractional concentration of fetal DNA can be estimated by the fractional concentration of chromosome Y sequences in these samples. There was a significant correlation between $\Delta F_{(18-Ref)}$ and the fractional concentration of chromosome Y sequences (r=0.879, Spearman correlation). These results suggest that the degree of shortening in the size distribution of chromosome 18 sequences in maternal plasma is correlated with the fractional concentration of fetal DNA in the maternal plasma in trisomy 18 pregnancies.

The cases below the diagnostic cutoff are represented by an open circle whereas the cases having a difference of more than the cutoff are represented by filled circles. The two cases which had $\Delta F$ values less than the diagnostic cutoff (0.0003) (represented by open circles) had relatively lower fractional concentrations of fetal DNA when compared with those with $\Delta F$ values greater than 0.0003 (represented by filled circles). The low fractional fetal DNA concentrations might be the reason why these two cases were missed in the analysis performed in FIG. 18. Accordingly, in one embodiment, if fetal concentration is low in a sample, the classification might be disregarded or redone.

Figure 23C:
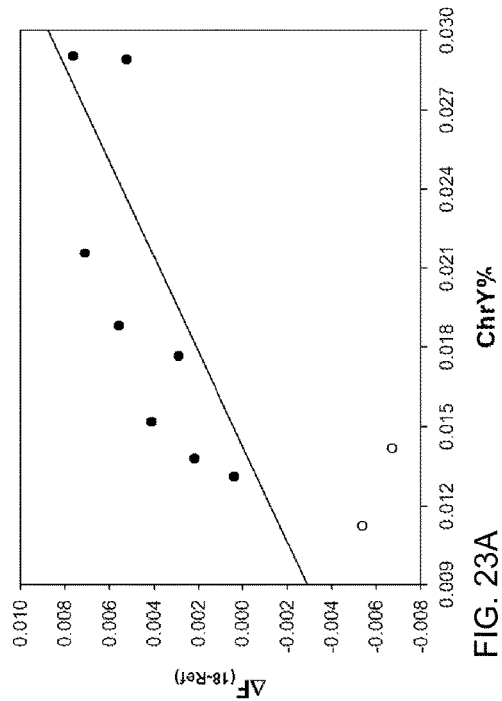
Figure 23B:
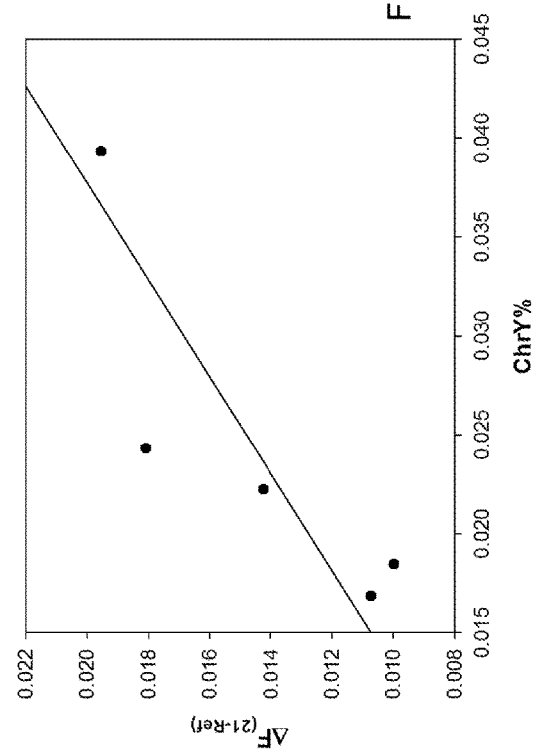

FIG. 23B shows a correlation between $\Delta F_{(21-Ref)}$ (chromosome 21 vs. reference chromosomes) and fetal DNA concentration. Five of the nine T21 cases were carrying male fetuses. There was a significant correlation between the value of $\Delta F_{(21-Ref)}$ and the fractional concentration of chromosome Y sequences (r=0.9, Spearman correlation).

FIG. 23C shows a correlation between $\Delta F_{(13-Ref)}$ (chromosome 13 vs. chromosomes 3, 4, 5 and 6) and fetal DNA concentration. Fourteen of the twenty-three trisomy 13 cases were carrying male fetuses. The fractional concentration of fetal DNA can be estimated by the fractional concentration of chromosome Y sequences in the samples. There was a positive correlation between $\Delta F_{(13-Ref)}$ and fractional concentration of chromosome Y sequences (r=0.644, Spearman correlation). The case which has a $\Delta F_{(13-Ref)}$ below the diagnostic cutoff (0.0038) is represented by an open circle. The low fractional fetal DNA concentrations might be the reason why this case had been missed in the analysis performed in FIG. 21.

IX Comparison of Size Analysis and a Molecular Counting Method

FIG. 24 shows a comparison of the accuracies of an embodiment of the present invention and another method for the noninvasive detection of fetal aneuploidies (trisomy 13 and trisomy 18) using maternal plasma DNA analysis. This example illustrates a comparison of embodiments using size versus a method based on molecular counting (U.S. patent application Ser. No. 11/701,686; Chiu et al Trends Genet 2009; 25: 324-331; Chiu et al Proc Natl Acad Sci USA 2008; 105: 20458-20463; Fan et al Proc Natl Acad Sci USA 2008; 105: 16266-16271; US Patent Publication 2009/0029377).

Eight maternal plasma samples (two euploid, two trisomy 18, and four trisomy 13) were analyzed using the method described by Chiu et al (Proc Natl Acad Sci USA 2008; 105: 20458-20463). For each case, the previously reported molecular counting method using z-score by Chiu et al with molecular counting was compared with the results of embodiments based on size analysis.

For the calculation of the z-score, the percentage representation of the chromosome of interest was first calculated for each case. Then, the mean and standard deviation of chromosomal representation was calculated for the reference cases. In this data set, cases 1, 2, 5, 6, 7 and 8 were used as the reference group for a calculation of the mean and standard deviation of the chromosome 18 representation. Cases 1, 2, 3 and 4 were used as the reference group for a calculation of the mean and standard deviation of the chromosome 13 representation. The z-score is defined as the number of standard deviations from the mean of the reference group. Significant overrepresentation of a chromosome is defined as a z-score of >3. Cases 3 and 4 were carrying trisomy 18 fetuses and the chromosome 18 fragments were overrepresented in their plasma. Cases 5, 6, 7 and 8 were carrying trisomy 13 cases, but only cases 5 and 7 showed an overrepresentation of chromosome 13 in their plasma. Cases 6 and 8 did not show significant overrepresentation of chromosome 13 in maternal plasma despite carrying trisomy 13 fetuses.

Significant shortening of the DNA fragments size of a chromosome was detected by comparing the size of all the fragments aligned to a particular chromosome to those aligned to a reference chromosome. The Mann-Whitney test was used for the comparison, and a P-value of <0.0001 was defined as the presence of a significant difference. For the analysis of the size of chromosome 13 fragments, the reference chromosome was chromosome 5. For all the cases carrying a euploid or trisomy 18 fetus, the fragment size of chromosome 13 was not significantly different from that of chromosome 5. For the four cases carrying trisomy 13 fetuses, the chromosome 13 fragments were significantly shorter than chromosome 5 fragments, implying that the fragment size of chromosome 13 was shortened compared with the non-trisomy 13 cases. Thus, all four trisomy 13 cases were correctly identified by the present invention, compared with two out of four by the z-score method.

For the analysis of the size of chromosome 18 fragments, the reference chromosome was chromosome 12. For all the cases carrying a euploid or trisomy 13 fetus, the fragment of chromosome 18 was significantly longer than the chromosome 12 fragments. For the two cases carrying trisomy 18 fetuses, the sizes of chromosome 18 fragments were not significantly different from those of chromosome 12 fragments, implying that the fragment size of chromosome 18 was shortened when compared with cases carrying non-trisomy 18 fetuses. In other words, both trisomy 18 cases were correctly classified.

X. Detection of Polymorphisms and Diagnosis of Genetic Disorders

Size analysis of maternal plasma DNA can also be used for the noninvasive detection of fetal genotype. The fetal genotype can be used to determine whether the fetus has inherited a mutated gene, has an imbalance of a particular allele, or other sequence imbalances or purposes. In such embodiments, one allele can be a reference genomic location (sequence) and a different allele can be the genomic location under test. Thus, any of the methods using a reference sequence can also be applied to determining a genotype and other sequence imbalances.

In one embodiment, a sequence imbalance (and thus possibly a genotype) can be determined by whether a size difference (imbalance) does or does not exist between alleles in the maternal sample (e.g. when the mother is heterozygous at the allele). For example, if there is no difference in the size profile between alleles in the sample, then the fetus may be determined to have the same genotype as the mother. As another example, if there is a difference in the size profile between alleles in the sample, then the fetus may be determined to have a genotype different from that of the mother.

In the following examples, the mother is heterozygous (i.e., with one copy of the N allele and one copy of the M allele, denoted by NM) for a particular locus. The letters N and M nominally represent the wildtype (N for normal) and mutant (M for mutant) alleles, respectively. However, the N and M alleles can correspond to any two different alleles, and not necessarily wildtype and/or mutant. In one embodiment, M can be considered the at-risk genomic sequence and N the reference sequence. With this context, one can understand the application of any of the above methods using a reference sequence to the determination of a genotype.

Figure 25:
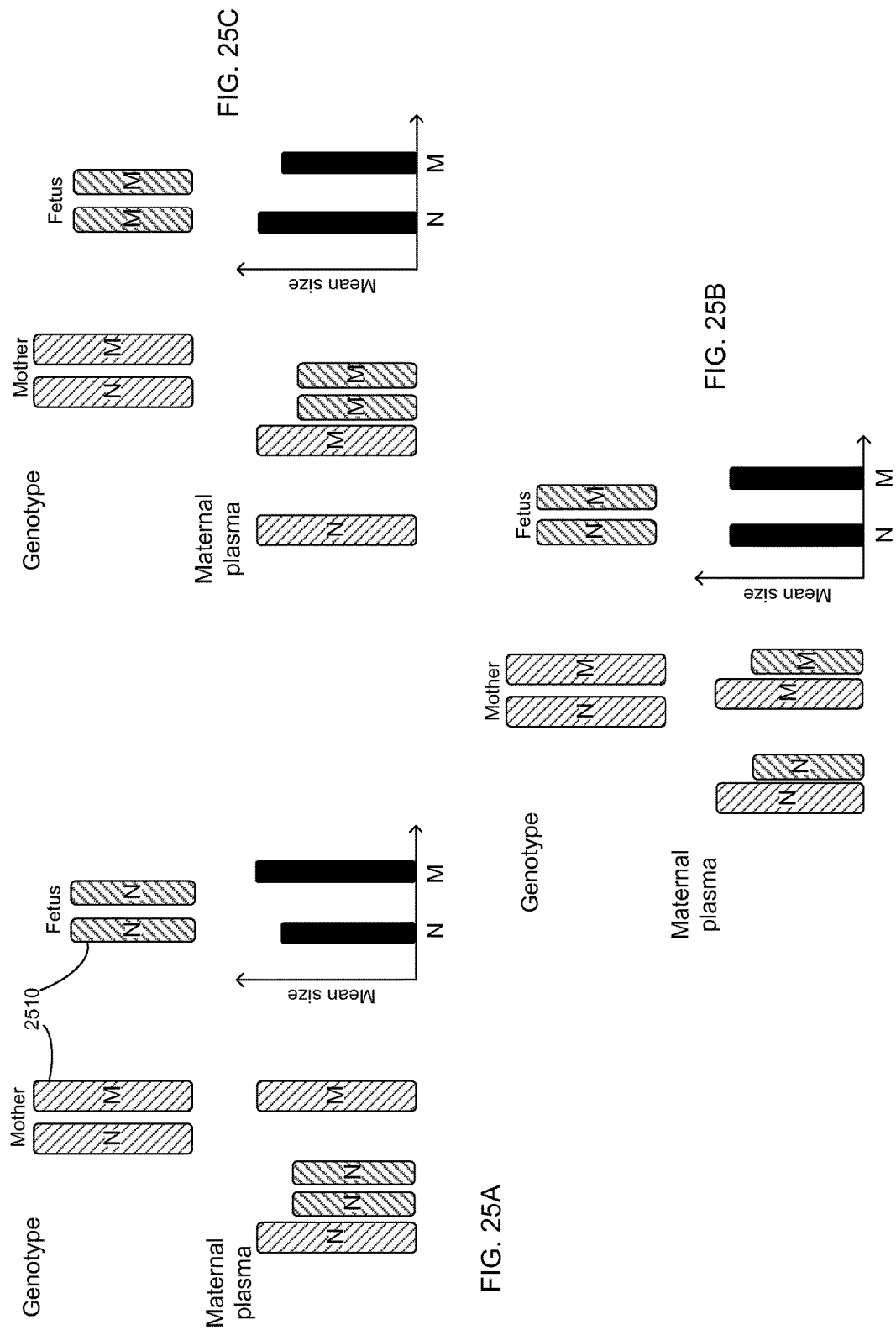
FIGS. 25A-25C show diagrams for different scenarios for genotypes of a pregnant woman and the fetus according to embodiments of the present invention.

In a non-pregnant woman, the average size of molecules carrying both of the two alleles would be the same. However, in the plasma of a pregnant woman, there is a mixture of DNA molecules from the mother and the fetus. The maternal-derived DNA molecules are longer than the fetal-derived ones. If the mother and fetus both have two alleles (i.e. both the N and M alleles), both of these alleles will have an equal contribution of long and short DNA molecules. Thus, the resulting size distribution of the N and M alleles will be the same. Conversely, if the genotypes of the mother and fetus are different, e.g. if the mother is NM and the fetus is MM, then the size distribution of the N and M alleles will be different. In other words, the size distribution of the two alleles in plasma would be affected by the genotype of the fetus. FIGS. 25A-25C show diagrams for different scenarios for genotypes of a pregnant woman and the fetus according to embodiments of the present invention.

In FIG. 25A, the fetus has a genotype of NN, and the genotype of the mother is NM. The length of a bar 2510 is an indication of an average (mean) size of fragments that are from one of the two alleles of the mother and of the fetus, respectively. As described above, a fetus has a smaller average size than a mother. Thus, the long bars represent maternal DNA and the short bars represent fetal DNA.

Since both the mother and the fetus contribute to the allele N whereas only the mother contributes to the allele M, the size distribution for molecules with the allele N would be shorter than that for molecules with the allele M. In other words, in a pregnant woman who has the genotype of NM, a shorter size distribution for allele N compared with allele M would imply the fetal genotype being NN. Thus, it can be identified that the fetus has two wildtype (N) alleles when the size distribution (e.g. mean size) of N is smaller than M by a certain cutoff (e.g. a percentage or absolute value).

In FIG. 25B, the fetus has the genotype of NM. Both the mother and fetus contribute alleles N and M. As a result, the size distributions for molecules with the alleles M and N are the same. In a pregnant woman who has the genotype of NM, the same size distributions for alleles M and N would indicate a fetal genotype of NM. Thus, it can be identified that the fetus has one wildtype (N) allele and one mutant (M) allele when the size distribution (e.g. mean size) of N is about equal to M within a certain cutoff (e.g. percentage or value).

In FIG. 25C, the fetus has the genotype of MM. Since both the mother and the fetus contribute to the allele M whereas only the mother contributes to the allele N, the size distribution for molecules with the allele M would be shorter than that for molecules with the allele N. In a pregnant woman who has the genotype of NM, the shorter size distribution for allele M than allele N would indicate the fetal genotype being MM. Thus, it can be identified that the fetus has two mutant (M) allele when the size distribution (e.g. mean size) of M is smaller than N by a certain cutoff (e.g. percentage or value).

The method can also be used to analyze situations where the mother is homozygous, e.g., NN or MM. If the fetus has a different genotype, the size distribution from the maternal sample will also change, and thus the genotype of the fetus can be determined. Also, if the size distribution does not change, then the genotype may be determined to be the same as the mother's, as described above for the case where the mother is heterozygous case.

In some embodiments, the determination of whether there is an imbalance, or otherwise, relative to the mother's genotype (e.g. one N for one M would imply no imbalance) can be performed with cutoff values. For example, if there is a large enough deviation (e.g. by percentage) from the mother's genotype, then the fetus can be determined to have inherited the allele with the smaller size distribution. In one embodiment, the cutoff value can be dependent on a percentage of fetal nucleic acids in the maternal sample. If there is a higher percentage of fetal nucleic acids, then a larger deviation would be expected, and thus a larger cutoff can be used (e.g. for the difference in size distribution for one allele relative to another). If there is a lower percentage of fetal nucleic acids, then a smaller deviation would be expected, and thus a smaller cutoff may be used.

In one embodiment, a genotype of the father may be used to determine which allele of the mother might have its size distribution changed due to the fetal nucleic acids. In instances where the father is homozygous for the genotype, this can allow for narrowing the possible fetal genotype to just what allele is inherited from the mother, since which one came from the father is known. After such a narrowing, the determination of the fetal genome might be more accurate since only two possibilities would need to be tested. In one implementation, a same cutoff value is used regardless of which genotype is inherited from the father. In another implementation, a different cutoff can be used.

In various embodiments, any of the size distributions mentioned herein may be used in such sequence imbalance determinations. In some embodiments, an accuracy level may also be provided. For example, a classification of "undetermined" may also be used, besides an imbalance and a balance classification. In this manner, some determinations may be determined with high confidence, whereas values in a middle region may require further data points.

XI. Size Analysis for Fetal Haplotype Inheritance

The application of size analysis can further be extended to determine which maternal haplotype is passed onto the fetus. A haplotype can refer to alleles at multiple loci. A definition of the term "haplotype" can be found in the Definitions section of the present application. The fetal haplotype can be used to determine whether the fetus has inherited a mutated gene, has an imbalance of a particular allele, or other purposes. Thus, the haplotype may be used in a similar manner as the genotype, but since there are more loci, a smaller volume of blood sample may be used to achieve the same, or even better, statistical confidence of determining the fetal haplotypes. In one aspect, the sequence imbalance can be determined relative to the mother's haplotype. Herein, a haplotype can be represented as a series of polymorphisms, for example SNPs, each at a particular location in the genome, at which a sequence variation is known.

In one embodiment, a method for determining a haplotype of a fetus by analyzing for sequence imbalances in the maternal plasma is provided. In one aspect, separation values (e.g. differences) in the size profiles between haplotypes is used to determine the sequence imbalance. In one embodiment, the haplotypes of the mother (e.g., Hap I and Hap II) are determined by analysis (e.g. sequencing (He D et al. Bioinformatics 2010; 26: i183-i190) or single molecule haplotyping (Ding C et al. Proc Natl Acad Sci USA 2003; 100: 7449-7453 and Xiao M et al. Nat Methods 2009; 6: 199-201) of a maternal sample (e.g. a sample that does not contain fetal nucleic acids). In another embodiment, the haplotype(s) of the mother can be determined using an analysis of the mother's parents, siblings, a previous child, or other relatives. In yet another embodiment, for polymorphisms at strong linkage disequilibrium, knowing the mother's genotype at one locus can imply a genotype at other loci, e.g., when alleles normally appear in a same sequence, i.e. haplotype. Thus, the mother's haplotype can implicitly be determined from one measure of genotype. The genotype at more than one locus can also be determined, where each determined genotype can imply genotypes at other loci and hence the haplotype is deduced.

In one embodiment, the father's genotype is also determined. This information can be used to determine if the father is homozygous or heterozygous at particular SNPs. A direct determination of the father's allele at each locus can be made. Accordingly, one can determine if each paternal allele is the same as the allele on Hap I or Hap II of the mother, termed type α or type β SNP.

In another embodiment, the father's haplotype is also determined. The father's haplotype can be determined by analysis (e.g. sequencing (He D et al. Bioinformatics 2010; 26: i183-i190) or single molecule haplotyping (Ding C et al. Proc Natl Acad Sci USA 2003; 100: 7449-7453 and Xiao M et al. Nat Methods 2009; 6: 199-201) of a paternal sample, or through an analysis of the father's parents, siblings, a previous child, or other relatives. Alternatively, for polymorphisms at strong linkage disequilibrium, knowing the father's genotype at one locus can imply a genotype at other loci, e.g., when alleles normally appear in a same sequence, i.e. haplotype. Thus, the father's haplotype can implicitly be determined from one measure of genotype. The genotype at more than one locus can also be determined, where each determined genotype can imply genotypes at other loci and hence the haplotype is deduced.

One application of such embodiments can be to determine if a sequence imbalance (e.g. by detecting a difference in size profile) does or does not exist in a maternal sample containing fetal nucleic acids by analyzing SNPs where both the father and mother are heterozygous. The fetus's genotype or haplotype is thereby deduced from whether the sequence imbalance does or does not exist.

Figure 26:
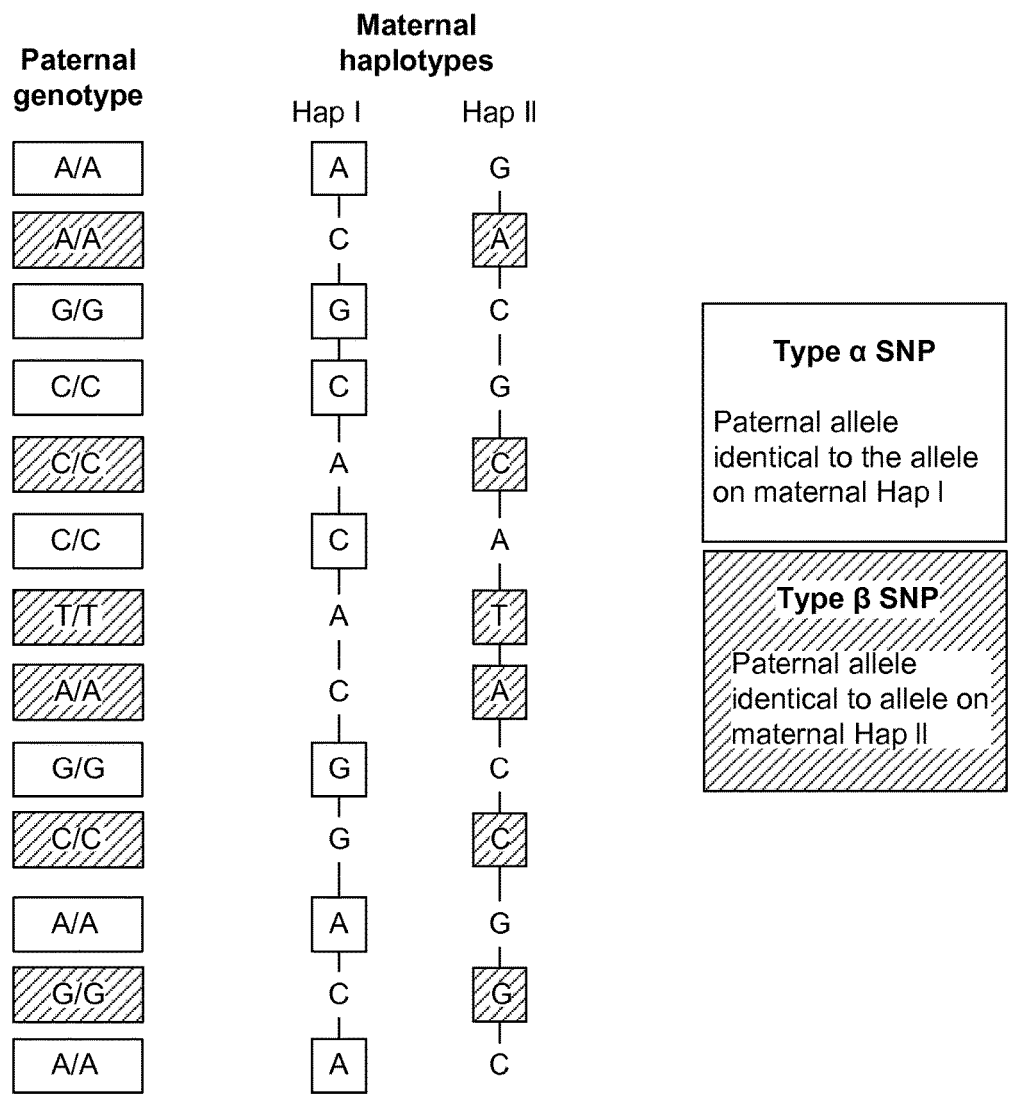
FIG. 26 shows an example where the mother is heterozygous and the father is homozygous according to embodiments of the present invention.

FIG. 26 shows an example where the mother is heterozygous and the father is homozygous at the SNP loci to be analyzed. To carry out the size analysis, the focus can be on a subset of SNPs which the mother is heterozygous and the father is homozygous. The two homologous chromosomes of the mother are termed Hap I and Hap II, respectively. For each of these SNPs, we can determine which one of the two maternal alleles is located on Hap I and which is on Hap II. A SNP is defined as type α if the paternal alleles are identical to the maternal allele on Hap I, and as type β if the paternal alleles are identical to the maternal allele on Hap II. A further description of determinations of a fetal genome can be found in the application "Fetal Genomic Analysis From A Maternal Biological Sample" referred to above.

Once the mother's haplotype and father's genotypes or haplotype are known, a size distribution for fragments associated with each SNP can be analyzed to determine the fetus's haplotype by identifying whether there is a sequence imbalance among the SNP subset. In an alternative embodiment, the paternal genotype or haplotype is not known for certain, one could nonetheless deduce using, for example, a statistical procedure the likely paternal genotype or haplotype, based on, for example, the frequencies of known genotypes or haplotypes in the tested population. A sequence imbalance (as determined via a size imbalance) is then determined for each SNP, e.g., as discussed in section X.

For example, if the father is homozygous for an allele on Hap I (type α), then either there will be no size imbalance (fetus inherits Hap II from mother and thus is heterozygous for Hap I and Hap II just like the mother) or there will be a size imbalance where Hap I has a smaller size distribution (fetus inherits Hap I from mother and thus is homozygous for Hap I). If the father is homozygous for Hap II (type β as described below), then either there will be no imbalance (fetus inherits Hap I from mother and thus is heterozygous for Hap I and Hap II) or there will be an imbalance where Hap II has a smaller size distribution (fetus inherits Hap II from mother and thus is homozygous for Hap I). An indeterminate classification can also be used, or varying levels of certainty between a balance and an imbalance. Typically, a similar cutoff would be used for either type. In various embodiments, any of the size distributions mentioned herein may be used.

In one embodiment, a size distribution for the fragments for each of a plurality of SNP location can be analyzed to determine the two haplotypes of the fetus. For example, a difference between the size distribution of fragments for the SNP alleles on one haplotype can be compared to the size distribution of SNP alleles on the other haplotype. The statistics can be analyzed in various ways, for example, by making a determination for each SNP and then taking the majority (balance, imbalance, and may be including indeterminate) as the haplotype. As another example, the sizes can be aggregated across SNPs (e.g. to obtain an average or median size distribution that is compared to a cutoff value). Or, a combination of the two can be used. Another implementation could be to use an extremum of the data points, e.g., the smallest difference for a particular SNP.

Figure 27:
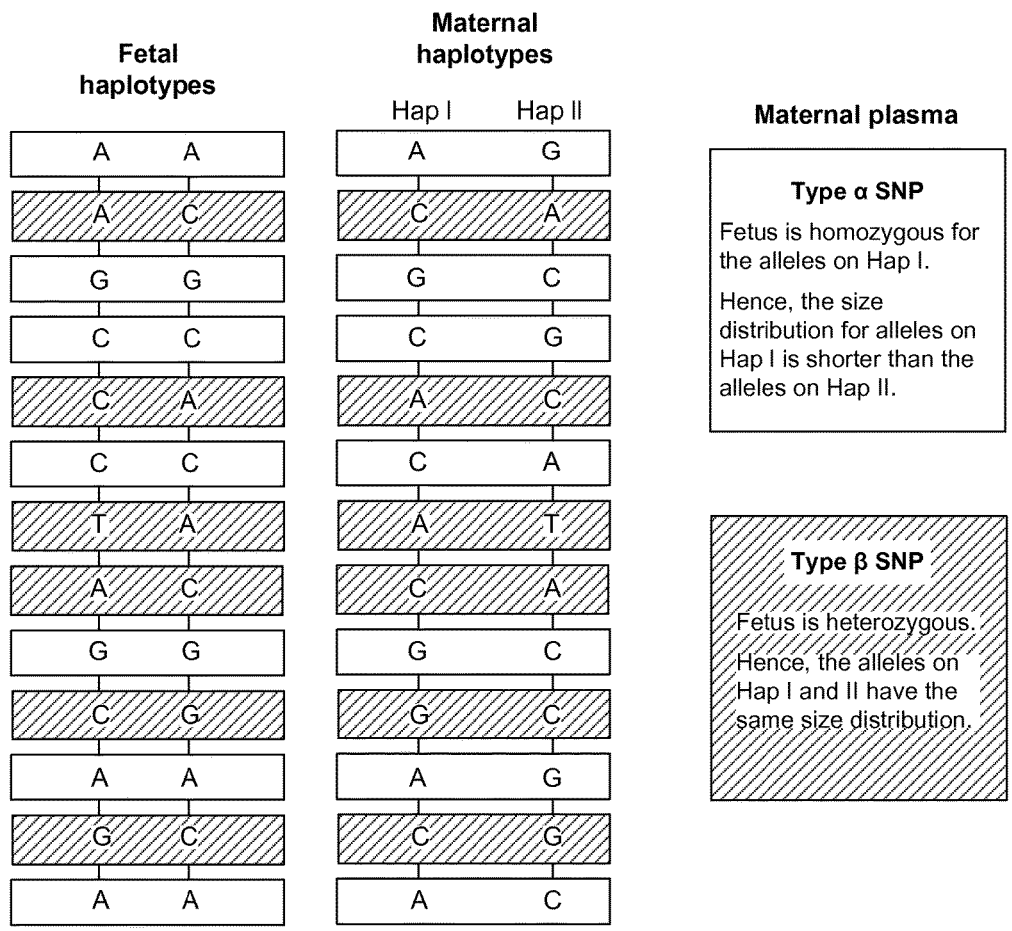
FIG. 27 shows an example where the fetus inherits Hap I from the mother when the parental haplotype is as shown in FIG. 26 according to embodiments of the present invention.

FIG. 27 shows an example where the fetus inherits Hap I from the mother when the paternal haplotype is as shown in FIG. 26. For type α SNPs (enclosed by non-shaded boxes), the fetus would have inherited alleles identical to the ones located on maternal Hap I from the father. Hence, the fetus would be homozygous for the alleles on Hap I. As a result the size distribution of the alleles on Hap I would be shorter than the allele on Hap II in maternal plasma. For type β SNPs (enclosed by shaded boxes), the fetus would have inherited alleles identical to those on the maternal Hap II from the father. Hence, the fetus would be heterozygous. As a result, the size distribution of the alleles on Hap I and Hap II would have the same size distribution in maternal plasma.

In one embodiment, SNPs of the same type (type α or type β) can be analyzed together. For type α SNPs, the size distribution of molecules carrying the alleles on Hap I would be shorter than the size distribution of molecules carrying the alleles on Hap II. For type β SNPs, the size distributions of molecules carrying the alleles on Hap I and Hap II would be the same. In other words, if the size distribution for molecules carrying Hap I is shorter than that for molecules carrying Hap II, the fetus is homozygous for Hap I. If the size distributions for molecules carrying Hap I and II are the same, the fetus is heterozygous.

EXAMPLE

The following experiment was used to test the accuracy of a fetal haplotype inheritance analysis. A couple, attending an obstetrics clinic for the prenatal diagnosis of β-thalassemia, was recruited. Blood samples were taken from the father and mother. For the mother, the blood sample was taken prior to chorionic villus sampling (CVS) at 12 weeks of gestation. Following CVS, a portion was stored for the experiment.

DNA was extracted from the buffy coats of the father and mother, and the CVS sample. These DNA samples were subjected to analysis by the Affymetrix Genome-Wide Human SNP Array 6.0 system to determine the genotypes of the father, mother and the fetus. In this experiment, the CVS data were used to deduce the maternal haplotype. However, in the clinical implementation of the test, the maternal haplotype could be deduced by other means as described above. The CVS data were also used to confirm the accuracy of the determination using methods herein, which do not require a CVS.

In the current illustration, we focus on an informative subset of SNPs in which the mother was heterozygous and the father was homozygous. In this subset of SNPs, the genotypes of the couple and the fetus were used for constructing the haplotypes of the mother. We defined that haplotype I (Hap I) to be the series of alleles that the mother had passed onto the fetus whereas haplotype II (Hap II) to be the series of alleles that the fetus did not receive from the mother.

Then, we divided the informative SNPs into two subtypes, namely type α and type β. For type α SNPs, paternal alleles were identical to the maternal allele on Hap I. For these SNPs, the fetus would have inherited the same allele (the allele on Hap I) from the parents and, hence, the fetus would be homozygous for the SNPs on Hap I. For type β SNPs, the paternal alleles were identical to the maternal allele on Hap II. For these SNPs, the fetus would have inherited the alleles on Hap I from the mother and different alleles (identical to the ones on Hap II) from the father and, hence, the fetus would be heterozygous.

DNA extracted from the plasma of the mother was subjected to massively parallel sequencing using the Illumina Genome Analyzer platform. Paired-end sequencing of the plasma DNA molecules was performed. Each molecule was sequenced at each end for 50 bp, thus totaling 100 bp per molecule. The two ends of each sequence were aligned to the non-repeat-masked human genome (Hg18 NCBI.36 downloaded from UCSC genome.ucsc.edu) using the SOAP2 program from the Beijing Genomics Institute at Shenzhen (soap.genomics.org.cn/) (Li R et al. Bioinformatics 2009, 25(15):1966-7)

In one embodiment, a statistical value of fraction of total length contributed by short fragments for haplotypes was used to determine which maternal haplotype was passed onto the fetus. As an example, chromosome 22 is used to illustrate how the size analysis can be used for deducing which maternal haplotype is passed onto the fetus. First, we divided chromosome 22 into several segments with each segment containing 50 informative SNPs in which the mother was heterozygous and the father was homozygous (chromosome 22 and the segments both being examples of sequences). For each segment, the DNA fragments (examples of molecules that are part of the sequences) covering these informative SNPs were divided into two groups, namely Hap I and Hap II, according to which of the two maternal haplotypes these fragments corresponded to. For each segment, the sum of total length of all fragments mapping to the maternal Hap I and maternal Hap II were determined. Then, similarly, the sum of total length of short fragments mapping to the maternal Hap I and Hap II in each segment were determined. For illustration purpose, fragments of 150 bp or shorter are defined as short in this example for the calculation of the total length of short fragments. From these lengths, the fractions of total length contributed by short fragments can be calculated for the DNA fragments mapping to Hap I and Hap II within each segment.

FIG. 28 shows a table illustrating a size analysis for type α SNPs on chromosome 22 according to embodiments of the present invention. $\Delta F_{(Hap\ I-Hap\ II)}$ represents the difference in the fraction of total length contributed by short fragments between Hap I and Hap II. When the last segment which consisted of only 28 SNPs is excluded, $\Delta F_{(Hap\ I-Hap\ II)}$ ranged from 0.0288 to 0.0701. The positive values of $\Delta F_{(Hap\ I-Hap\ II)}$ signify that the F values of Hap I are always greater than that of Hap II. As the F value is defined as the fraction of total length contributed by short fragments, a higher F value indicates that a higher fraction of total length is contributed by short fragments. In other words, these results indicate that the DNA fragments carrying alleles on Hap I are shorter than those carrying alleles on Hap II for each of the regions consisting of 50 SNPs being analyzed. This indicates that the size distribution of Hap I is shorter than that of Hap II. Therefore, we can deduce that the fetus is homozygous for the alleles on Hap I. As mentioned above, in one embodiment, a classification can be made for each segment based on the separation value (e.g. ΔF) between the two genomic locations in Hap I and Hap II, and then a total classification can be made based on the respective segment classifications. In another embodiment, a total separation value (e.g. an average separation value) can be determined from the separation values for each segment, and this total statistical value can be used to determine a classification.

In one embodiment, a cutoff of about 0.02 may be used to determine if an imbalance exists. If a median or average of ΔF was used, a larger cutoff could be used and still be accurate. Cutoffs may also be used for indeterminate results, e.g., a region between 0.015 and 0.025 may be indeterminate and in need of further analysis.

FIG. 29 shows a table illustrating a size analysis for type β SNPs on chromosome 22 according to embodiments of the present invention. ΔF(Hap I-Hap II) represents the difference in the fraction of total length contributed by short fragments for Hap I and Hap II. The ΔF(Hap I-Hap II) values ranged from −0.0203 to 0.0207 with a median of 0.0003. The small ΔF(Hap I-Hap II) value is compatible with the same size distribution for fragments mapping to Hap I and Hap II. Thus, we can deduce that the fetus is heterozygous for Hap I and Hap II. As type β SNPs are defined as SNPs at which the paternal alleles are identical to the maternal alleles on Hap II, this result implies that the fetus has inherited Hap I from the mother.

Figure 30:
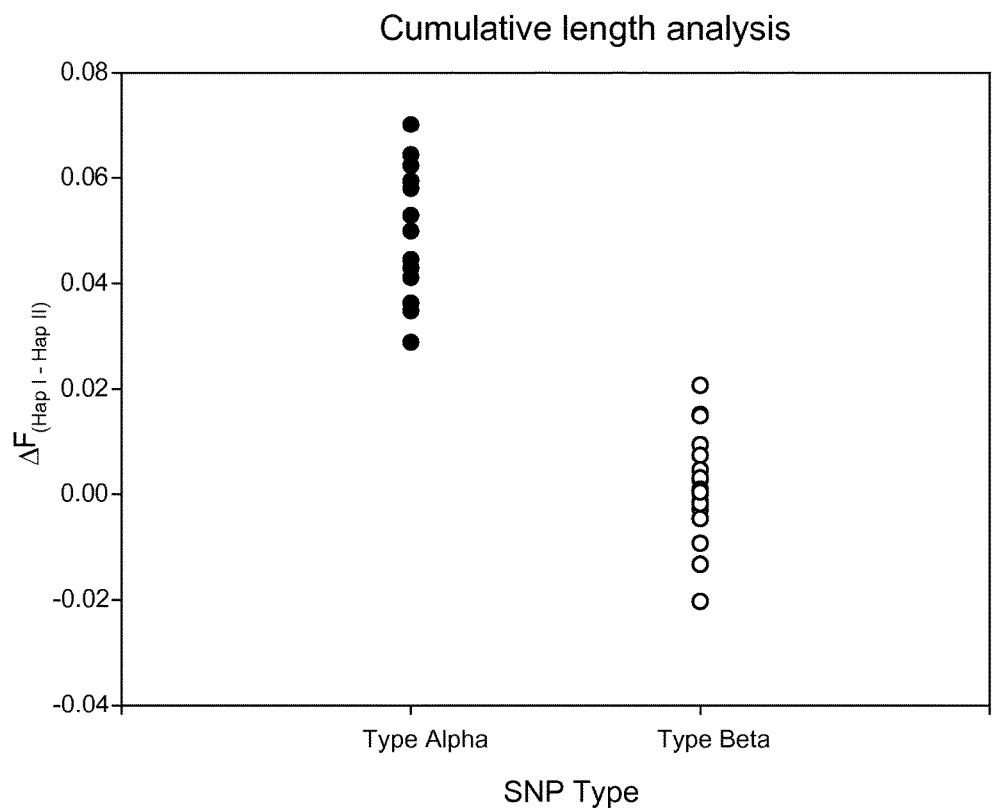
FIG. 30 shows a plot of $\Delta F_{(Hap\ I-Hap\ II)}$ for type α and type β SNPs on chromosome 22 according to embodiments of the present invention.

FIG. 30 shows a plot of ΔF(Hap I-Hap II) for type α and type β SNPs on chromosome 22 according to embodiments of the present invention. For type α SNPs, the size distribution of Hap I fragments is shorter than that of Hap II fragments, which results in values of ΔF(Hap I-Hap II) greater than zero. For type β SNPs, there is no difference between the size distribution of Hap I and Hap II fragments; therefore, the ΔF(Hap I-Hap II) values cluster around 0. Using a cutoff of 0.025, a ΔF(Hap I-Hap II) analysis can correctly deduced the inheritance of Hap I by the fetus for all the 13 type α segments and 21 type β segments.

XII. Example of Using Targeted Sequencing

The following example demonstrates that a size-based diagnostic approach of embodiments of the present invention can be usable in a targeted sequencing format. In such a format, genomic regions of diagnostic interest are specifically targeted for the sequencing. This format has the advantage that the sequencing is focused on the region of interest, in contrast to the situation involving random sequencing, where some of the sequencing power is used for regions which are not immediately relevant to the diagnostic application. Thus, the targeted sequencing format can be expected to increase the throughput and reduce the cost of the system. Targeted sequencing can be performed using any format known to those of skill in the art, including a solution-phase capture system (e.g. the Agilent SureSelect system), a solid-phase capture system (e.g. the Roche NimbleGen system) or by target-specific amplification (e.g. the RainDance system).

Blood samples were collected from eight pregnant women during their first trimester. DNA from 3.2 mL of plasma was extracted for each case by the DSP DNA Blood Mini Kit (Qiagen). Karyotyping performed on the chorionic villus samples (collected after maternal blood samples had been taken) indicated that four fetuses had T21 (UK229, UK510, UK807, PW421), while the other four were euploid males (PW226, PW263, PW316, PW370).

5 to 30 ng of plasma DNA for each case was used for DNA library construction by the paired-end sample preparation kit (Illumina) according to the manufacturer's protocol of Chromatin Immunoprecipitation Sequencing sample preparation. The adapter-ligated DNA was purified directly using spin columns provided in a QIAquick PCR purification kit (Qiagen), without further size selection. The adapter-ligated DNA was then amplified using a 15-cycle PCR with standard primers. The primers were PCR Primer PE 1.0 and 2.0 from Illumina. The DNA libraries were quantified by using a NanoDrop ND-1000 spectrophotometer (NanoDrop Technologies) and run on a 2100 Bioanalyzer, using a DNA 1000 kit (Agilent), to check for size distribution. 0.6 to 1 µg of an amplified plasma DNA library was generated for each sample in an average size of about 290 bp.

The SureSelect Human All Exon capture library was obtained from Agilent and covered 37.8 Mb of human exons (catalog number: 5190-2310). For all eight cases in this study, 500 ng of the amplified plasma DNA library of each case was incubated with the capture probes for 24 hours at 65° C., according to the manufacturer's instruction. After hybridization, the captured targets were selected by pulling down the biotinylated probe/target hybrids by using streptavidin-coated magnetic beads (Dynal DynaMag-2 Invitrogen), and purified with the MinElute PCR Purification Kit (Qiagen). Finally, the targeted DNA libraries were enriched by 12-cycle PCR amplification with SureSelect GA PE primers from Agilent. The PCR products were purified by a QIAquick PCR Purification Kit (Qiagen).

Eight pairs of libraries with and without target-enrichment were loaded onto 16 lanes of two flow cells, and then sequenced by a Genome Analyzer IIx (Illumina) using a 36-bp×2 paired end format. All 36-bp sequenced reads were aligned to the unmasked human reference genome (Hg18) (genome.ucsc.edu), using the Short Oligonucleotide Alignment Program 2 (soap.genomics.org.cn/). The fragment size of paired-end reads was defined ranging from 40 bp to 600 bp. The size of each sequenced DNA fragment was inferred from the coordinates of the outermost nucleotides at both ends.

Size Analysis for Prenatal Detection of Fetal Trisomy 21

In this example, fractions of total length contributed by short fragments were calculated for chromosome 21 and the reference chromosomes, represented by $F_{21}$ and $F_{ref}$, respectively. The reference chromosomes consisted of all autosomes except chromosomes 13, 18 and 21. The total length was calculated by the summation of length for all DNA fragments of 600 bp or less. A difference in the fraction of length contributed by short fragments between chromosome 21 and the reference chromosomes ($\Delta F$) was calculated as $F_{21}-F_{ref}$.

FIG. 31A is a table that provides a size analysis of plasma DNA without target enrichment according to embodiments of the present invention. Various columns provide total length for fragments ≤150 bp for chromosome 21, total length for fragments ≤600 bp for chromosome 21, and the ratio of the two as $F_{21}$. Other columns provide total length for fragments ≤150 bp for the reference chromosomes, total length for fragments ≤600 bp for the reference chromosomes, and the ratio of the two as $F_{ref}$. The last column is the difference between the two fractions, $\Delta F$.

FIG. 31B is a table that provides a size analysis of plasma DNA with target enrichment according to embodiments of the present invention. The columns of FIG. 31B have the same data format as the table for FIG. 31B.

Figure 32:
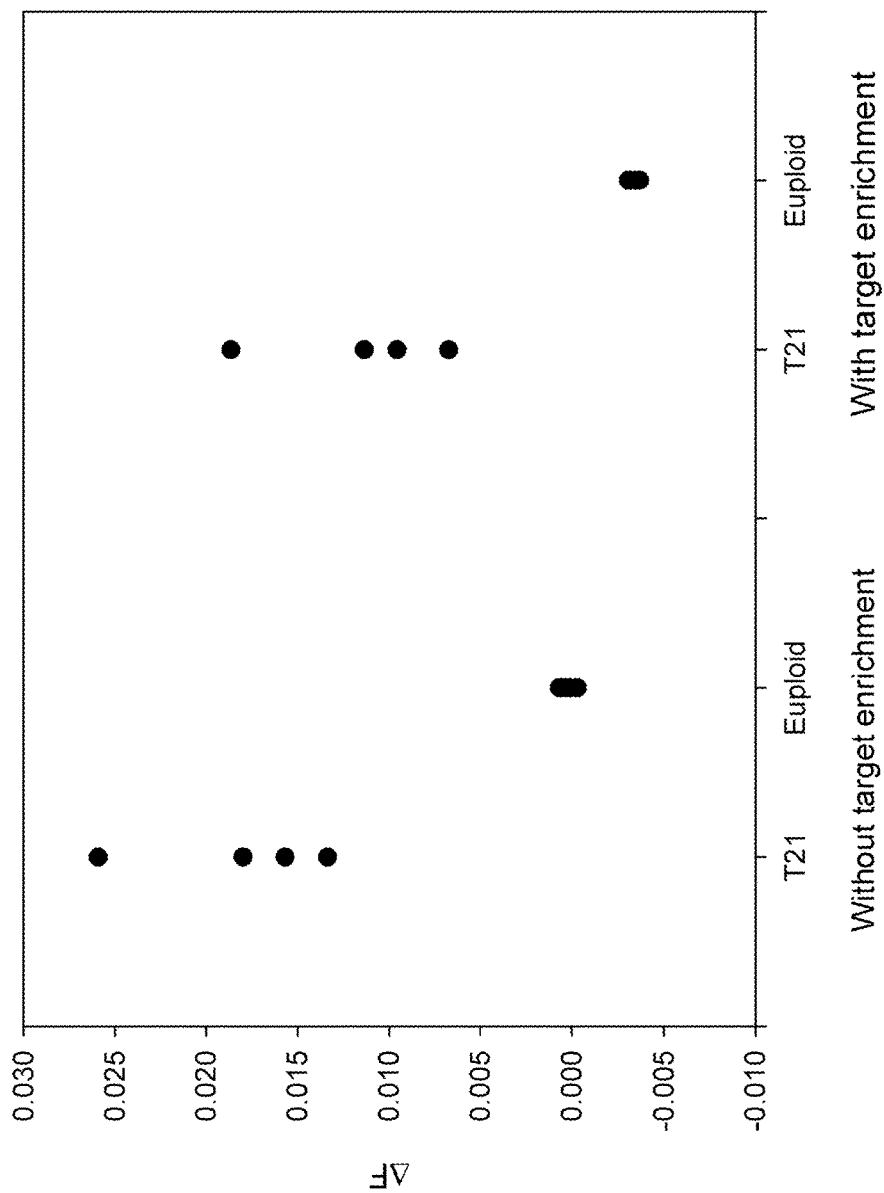
FIG. 32 is a plot of $\Delta F$ for the T21 and euploid samples with and without target enrichment according to embodiments of the present invention.

FIG. 32 is a plot of $\Delta F$ for the T21 and euploid samples with and without target enrichment. For the samples without target enrichment, using a cutoff value of 0.005 for $\Delta F$, the plasma samples from T21 and euploid pregnancies can be differentiated with 100% accuracy. For the samples with target enrichment, using a cutoff value of 0.004 for $\Delta F$, the plasma samples from T21 and euploid pregnancies can be differentiated with 100% accuracy. This example demonstrates that the size-based analysis can be performed using targeted sequencing. For the detection of T21, it may be advantageous to use targeted sequencing for chromosome 21 and a reference chromosome, such that 50% of the sequencing is directed to the former and the rest is directed to the latter. Such a design can reduce the waste of sequencing power to regions that are not immediately relevant to the detection of T21. Such a design can allow samples from multiple patients to be sequenced using multiplex sequencing (e.g. by using indexed or barcoded sequencing).

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive or an entire computer system), and may be present on or within different computer program products within a system or network. A computer system may include a monitor, printer, or other suitable display for providing any of the results mentioned herein to a user.

An example of a computer system is shown in FIG. 33. The subsystems shown in FIG. 33 are interconnected via a system bus 3375. Additional subsystems such as a printer 3374, keyboard 3378, fixed disk 3379, monitor 3376, which is coupled to display adapter 3382, and others are shown. Peripherals and input/output (I/O) devices, which couple to I/O controller 3371, can be connected to the computer system by any number of means known in the art, such as serial port 3377. For example, serial port 3377 or external interface 3381 can be used to connect the computer apparatus to a wide area network such as the Internet, a mouse input device, or a scanner. The interconnection via system bus allows the central processor 3373 to communicate with each subsystem and to control the execution of instructions from system memory 3372 or the fixed disk 3379, as well as the exchange of information between subsystems. The system memory 3372 and/or the fixed disk 3379 may embody a computer readable medium. Any of the values mentioned herein can be output from one component to another component and can be output to the user.

A computer system can include a plurality of the same components or subsystems, e.g., connected together by external interface 3381 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

All publications, patents, and patent applications cited herein are hereby incorporated by reference in their entirety for all purposes.

What is claimed is:

1. A method for performing prenatal diagnosis of a sequence imbalance in a biological sample obtained from a female subject pregnant with a fetus, wherein the biological sample includes a mixture of cell-free DNA molecules that are part of DNA sequences of a human genome, the biological sample including DNA molecules from the fetus and the female subject, the method comprising:

extracting the mixture of cell-free DNA to obtain the biological sample;

for each of a plurality of the DNA molecules in the biological sample:
  measuring a size of the DNA molecule, wherein measuring the size of the DNA molecule comprises:
    paired-end sequencing of the DNA molecule to obtain two sequence reads, wherein the paired-end sequencing is part of performing a random sequencing of the plurality of DNA molecules in the biological sample, and
  identifying which nucleic acid sequence in the human genome the DNA molecule is derived from, wherein identifying which DNA sequence the DNA molecule is derived from includes:
    aligning, by a computer system, the two sequence reads to the human genome;

calculating, by the computer system, a first statistical value from the sizes of DNA molecules from a first sequence;

identifying one or more reference sequences;

calculating, by the computer system, a second statistical value from the sizes of DNA molecules from the one or more reference sequences;

determining a parameter using the first statistical value and the second statistical value, the parameter being a difference or a ratio of the first statistical value and the second statistical value; and determining a classification of whether a sequence imbalance exists for the first sequence based on a comparison of the parameter to a cutoff value.

2. The method of claim 1, wherein the first statistical value includes the median or average size of the measured sizes for the DNA molecules from the first sequence.

3. The method of claim 1, wherein the first sequence is a chromosome and the sequence imbalance is a fetal chromosomal aneuploidy.

4. The method of claim 3, wherein the one or more reference sequences comprise one chromosome.

5. The method of claim 3, wherein the one or more reference sequences are a plurality of chromosomes.

6. The method of claim 1, wherein the biological sample includes blood, plasma, serum, maternal blood containing fetal cells, fetal cells obtained from maternal blood, urine, saliva, or uterine lavage fluid.

7. The method of claim 1, wherein the plurality of the DNA molecules includes at least one million DNA molecules.

8. The method of claim 1, further comprising:
collecting a blood sample from the female subject, and extracting plasma from the blood sample to obtain the biological sample.

9. The method of claim 1, further comprising displaying, by the computer system, the classification of whether the sequence imbalance exists for the first sequence.

10. The method of claim 1, wherein measuring the size of the DNA molecule comprises:
determining a second sequence and a third sequence from the two sequence reads, the second sequence corresponding to one end of the DNA molecule and the third sequence corresponding to the other end of the DNA molecule, mapping the second sequence and the third sequence to a reference genome to obtain genomic coordinates of the second sequence and the third sequence, and subtracting the genomic coordinates of the second sequence from the third sequence to obtain the size of the DNA molecule.

11. The method of claim 1, further comprising:
determining a first amount of sequences identified as aligning to the first sequence of the human genome;
determining a second amount of sequences identified as aligning to one or more second sequences;
using the first amount and the second amount to determine another parameter;
comparing the other parameter to one or more second cutoff values to determine another classification of whether the sequence imbalance exists for the first sequence.

12. The method of claim 11, further comprising:
comparing the classification determined using the first statistical value and the second statistical value to the other classification determined using the first amount and the second amount.

13. The method of claim 1, wherein the one or more reference sequences have a GC content that is similar to a GC content of the first sequence.

14. The method of claim 13, further comprising:
calculating the GC content of the one or more reference sequences; and
calculating the GC content of the first sequence.

15. The method of claim 13, wherein the GC content of the one or more reference sequences and the GC content of the first sequence are obtained for a particular sequencing platform.

* * * * *